(12) United States Patent
Kohn et al.

(10) Patent No.: US 10,940,235 B2
(45) Date of Patent: Mar. 9, 2021

(54) BIOCOMPATIBLE IMPLANTS FOR NERVE RE-GENERATION AND METHODS OF USE THEREOF

(71) Applicant: Rutgers, The State University of New Jersey, New Brunswick, NJ (US)

(72) Inventors: Joachim B. Kohn, Piscataway, NJ (US); Basak Clements, Newbury Park, CA (US); Mindy Ezra Sadik, Gainesville, FL (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 338 days.

(21) Appl. No.: 15/566,552

(22) PCT Filed: Apr. 15, 2016

(86) PCT No.: PCT/US2016/027858
§ 371 (c)(1),
(2) Date: Oct. 13, 2017

(87) PCT Pub. No.: WO2016/168669
PCT Pub. Date: Oct. 20, 2016

(65) Prior Publication Data
US 2018/0280567 A1 Oct. 4, 2018

Related U.S. Application Data

(60) Provisional application No. 62/148,087, filed on Apr. 15, 2015.

(51) Int. Cl.
*A61L 27/18* (2006.01)
*A61B 17/11* (2006.01)
(Continued)

(52) U.S. Cl.
CPC .......... *A61L 27/18* (2013.01); *A61B 17/1128* (2013.01); *A61L 27/16* (2013.01);
(Continued)

(58) Field of Classification Search
CPC .................................................. A61B 17/1128
See application file for complete search history.

(56) References Cited

U.S. PATENT DOCUMENTS

| 5,713,867 A | 2/1998 | Morris |
| 6,716,225 B2 | 4/2004 | Li et al. |

(Continued)

FOREIGN PATENT DOCUMENTS

| EP | 2228036 A1 | 9/2010 |
| JP | 2000-143531 A | 5/2000 |

(Continued)

OTHER PUBLICATIONS

Magno et al., "Synthesis, degradation and biocompatibility of tyrosine-derived polycarbonate scaffolds", 2010, J. Mater. Chem., 20, 8885-8893.*

(Continued)

*Primary Examiner* — Diane D Yabut
(74) *Attorney, Agent, or Firm* — Fox Rothschild LLP

(57) ABSTRACT

A biocompatible nerve conduit for nerve re-generation, wherein a porous fiber tube is coated with a bioresorbable hydrogel, with the fibers being formed from a polymer that supports nerve regeneration by preferential adsorption of endogenous proteins and braided with pores in the range from 5 to 200 micrometers using a kink-resistant braiding pattern and the hydro gel coating material and thickness being selected to control the overall porosity, so that nutrients and oxygen can diffuse through said hydrogel coating but the infiltration of fibrous tissue through the coating is prevented.

16 Claims, 8 Drawing Sheets

(51) Int. Cl.
| | |
|---|---|
| *C08G 64/12* | (2006.01) |
| *A61L 27/20* | (2006.01) |
| *A61L 27/24* | (2006.01) |
| *A61L 27/52* | (2006.01) |
| *A61L 27/16* | (2006.01) |
| *A61L 27/34* | (2006.01) |
| *A61L 27/54* | (2006.01) |
| *A61L 27/56* | (2006.01) |
| *A61L 27/58* | (2006.01) |
| *C08G 69/40* | (2006.01) |
| *C08G 69/44* | (2006.01) |
| *C08G 64/18* | (2006.01) |
| *A61B 17/00* | (2006.01) |

(52) U.S. Cl.
CPC ............ *A61L 27/20* (2013.01); *A61L 27/24* (2013.01); *A61L 27/34* (2013.01); *A61L 27/52* (2013.01); *A61L 27/54* (2013.01); *A61L 27/56* (2013.01); *A61L 27/58* (2013.01); *C08G 64/12* (2013.01); *C08G 64/183* (2013.01); *C08G 69/40* (2013.01); *C08G 69/44* (2013.01); *A61B 2017/00004* (2013.01); *A61B 2017/00893* (2013.01); *A61B 2017/1132* (2013.01); *A61L 2400/06* (2013.01); *A61L 2430/32* (2013.01); *C08G 2210/00* (2013.01); *C08G 2230/00* (2013.01)

(56) References Cited

U.S. PATENT DOCUMENTS

| | | | |
|---|---|---|---|
| 6,913,765 | B2 | 7/2005 | Li et al. |
| 2004/0122454 | A1 | 6/2004 | Wang et al. |
| 2010/0291180 | A1 | 11/2010 | Uhrich |
| 2011/0125170 | A1* | 5/2011 | Hoke .................. A61L 27/3878 606/152 |
| 2012/0088832 | A1 | 4/2012 | Mayes et al. |
| 2012/0231519 | A1* | 9/2012 | Bushman ............... C08G 69/40 435/188 |
| 2014/0336681 | A1* | 11/2014 | Agarwal ............ A61B 17/1128 606/152 |
| 2014/0341842 | A1* | 11/2014 | Zarembinski ........ A61K 31/195 424/85.1 |

FOREIGN PATENT DOCUMENTS

| | | |
|---|---|---|
| JP | 2009153947 A | 7/2009 |
| JP | 2014-155622 A | 8/2014 |
| WO | 2013177147 A2 | 11/2013 |

OTHER PUBLICATIONS

English Tranlation of Sui et al. "Research of Modern Medical Care" (Jul. 31, 2008, China Science and Technology Press, pp. 322), tranlsation done in Dec. 2020, pp. 1-6.*

Ichihara et al: "Development of New Nerve Guide Tube for Repair of Long Nerve Defects", Tissue Engineering, Part C, Sep. 1, 2009, vol. 15, No. 3, pp. 387-402.

Ezra, et al: "Enhanced Femoral Nerve Regeneration After Tubulization with a Tyrosine-Derived Polycarbonate Terpolymer: Effects of Protein Adsorption and Independence of Conduit Porosity", Tissue Engineering, Part A, Nov. 12, 2013, vol. 20, Nos. 3 and 4, pp. 518-528.

Wang, et al: "Physical Properties and Biocompatibility of a Porous Chitosan-Based Fiber-Reinforced Conduit for Nerve Regeneration", Biotechnology Letters, Jul. 13, 2007, pp. 1697-1702.

Database WPI, Terumo Corp., Aug. 28, 2014, Week 201459, Thomson Scientific, London, GB: AN 2014-Q06965, XP002785605, & JP 2014 155622 A.

Sui, et al: "Research of Modern Medical Care", Jul. 31, 2008, China Science and Technology Press, pp. 322.

* cited by examiner

Figures
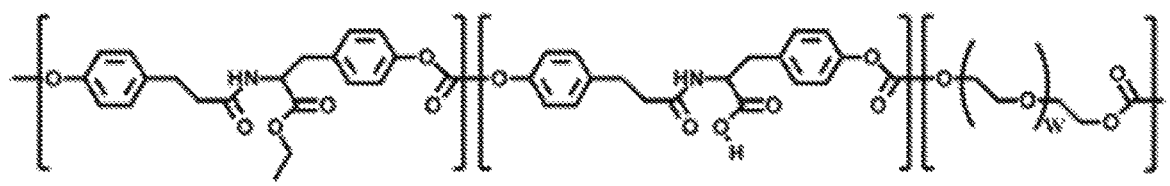
FIG. 1. Chemical structure of E10-0.5(1k) consisting of desaminotyrosyl tyrosine ethyl ester (DTE), desaminotyrosyl tyrosine (DT), and poly(ethylene glycol) (PEG).

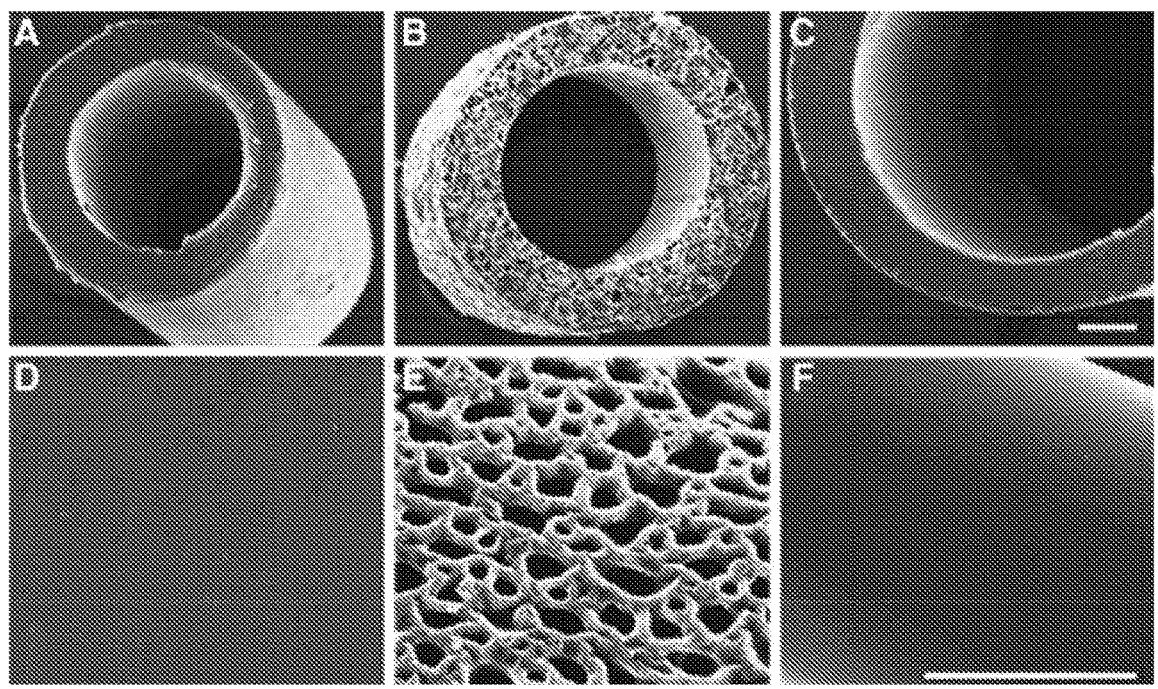
FIG. 2 Scanning electron microscope (SEM) images of conduits. Cross sections of (A, D) nonporous polyethylene (NP-PE) conduit, (B, E) porous E10-0.5(1K) [P-E10-0.5(1k)] conduit, and (C, F) nonporous E10-0.5(1k) [NPE10-0.5(1k)] conduit, respectively. Scale bar in each row: 100 μm.

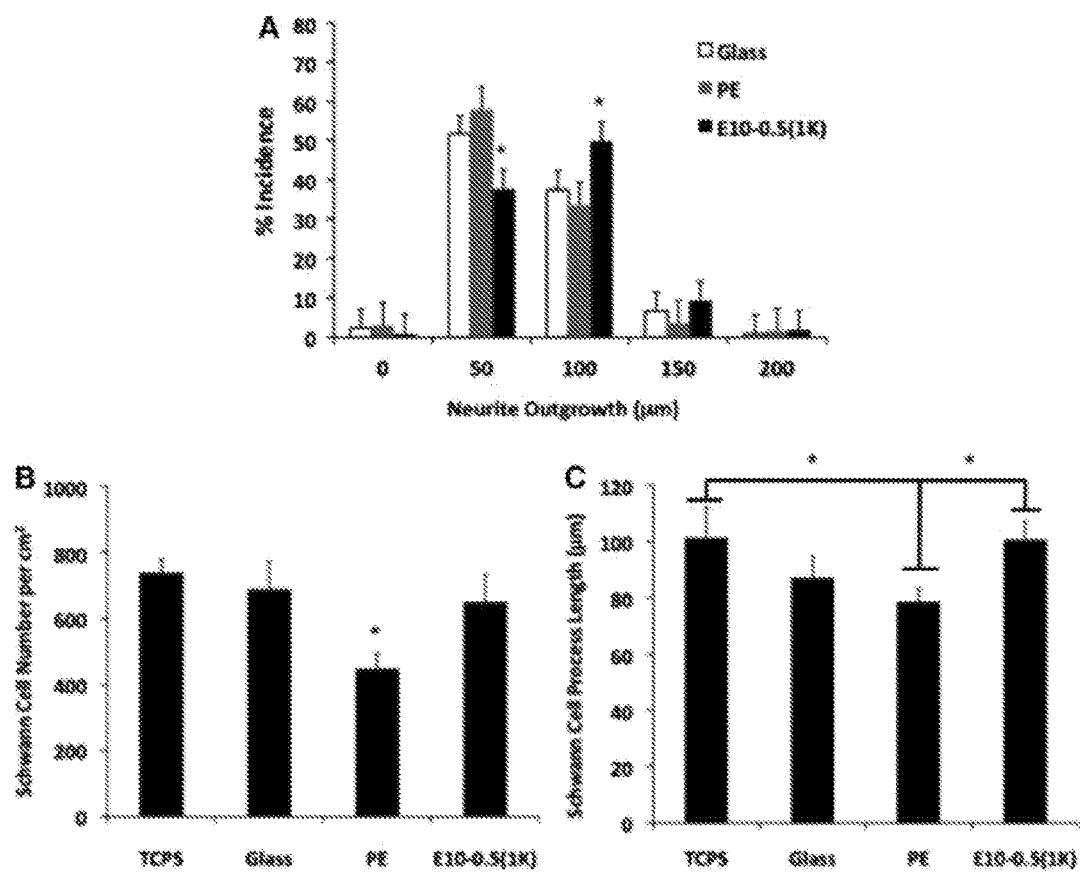
FIG. 3 In vitro evaluation of neurite outgrowth and Schwann cell proliferation and extension on two-dimensional (2D) films of E10-0.5(1k) and polyethylene (PE) in comparison with control substrates, tissue culture polystyrene (TCPS), and glass.

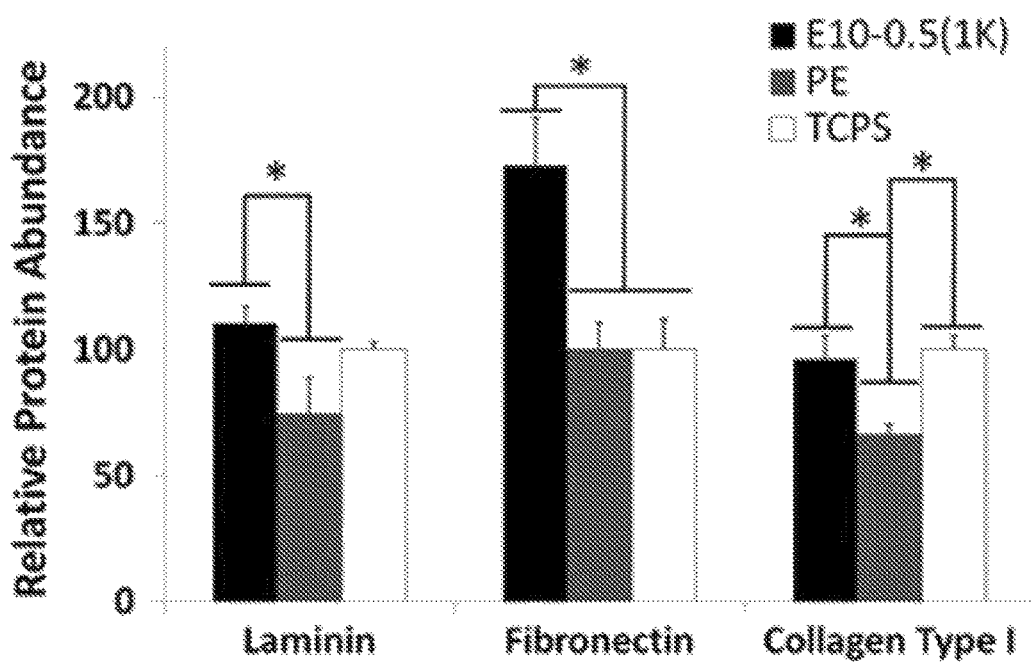
FIG. 4. Relative adsorption of neurosupportive extracellular matrix (ECM) proteins (laminin, fibronectin, and collagen type I) on 2D films of E10-0.5(1k) and PE in comparison with a control substrate, TCPS. (*$p < 0.05$, one-way analysis of variance with Tukey's post hoc test).

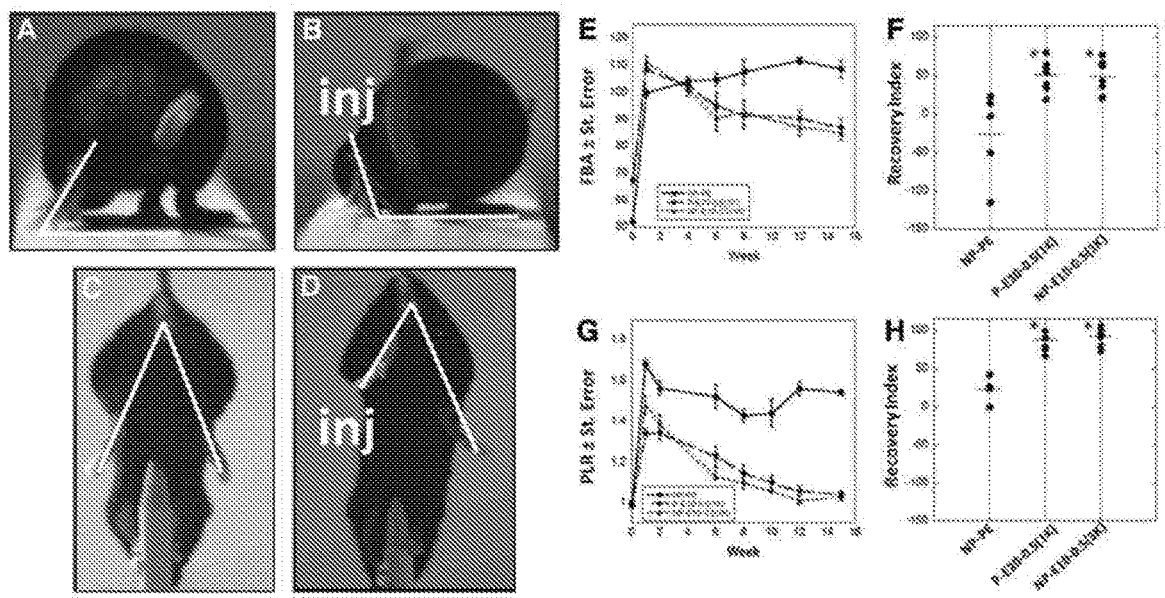

FIG. 5.

Video frames showing the functional measurements performed on mice following implantation of the conduit and metrics of functional recovery promoted by E10-0.5(1k) and NP-PE conduits in vivo. Frames A and C represent pre-injury measurements and frames B and D represent post-injury (inj) measurements. The white lines drawn in the video frames show the foot base angle (FBA) (A, B), and the limb lengths used for calculation of the protraction limb ratio (PLR) (C, D) (A) FBA of mice pre-injury averages 50–70°. (B) FBA of mice 1 week post-injury averages 90–110°. Functional recovery is denoted by a reduction in this degree angle. (C) The pencil grip test measures the PLR on a mouse pre-injury, where both limbs are similarly extended, giving a ratio of 1. (D) PLR on a mouse 1 week post-injury shows the disparity in limb protraction due to injury, resulting in a PLR>1. (E) FBA for a 15-week period following surgical insertion of nonporous PE conduits (NP-PE), porous E10-0.5(1K) conduits [P-E10-0.5(1K)], and nonporous E10-0.5(1K) conduits [NP-E10-0.5(1K)] pre-filled with saline. (F) Recovery index for FBA at week 15. Each dot represents one animal. (G) PLR for all conditions. (H) Recovery Index for PLR at week 15. (*p< 0.001, one-way analysis of variance with Tukey's post hoc test).

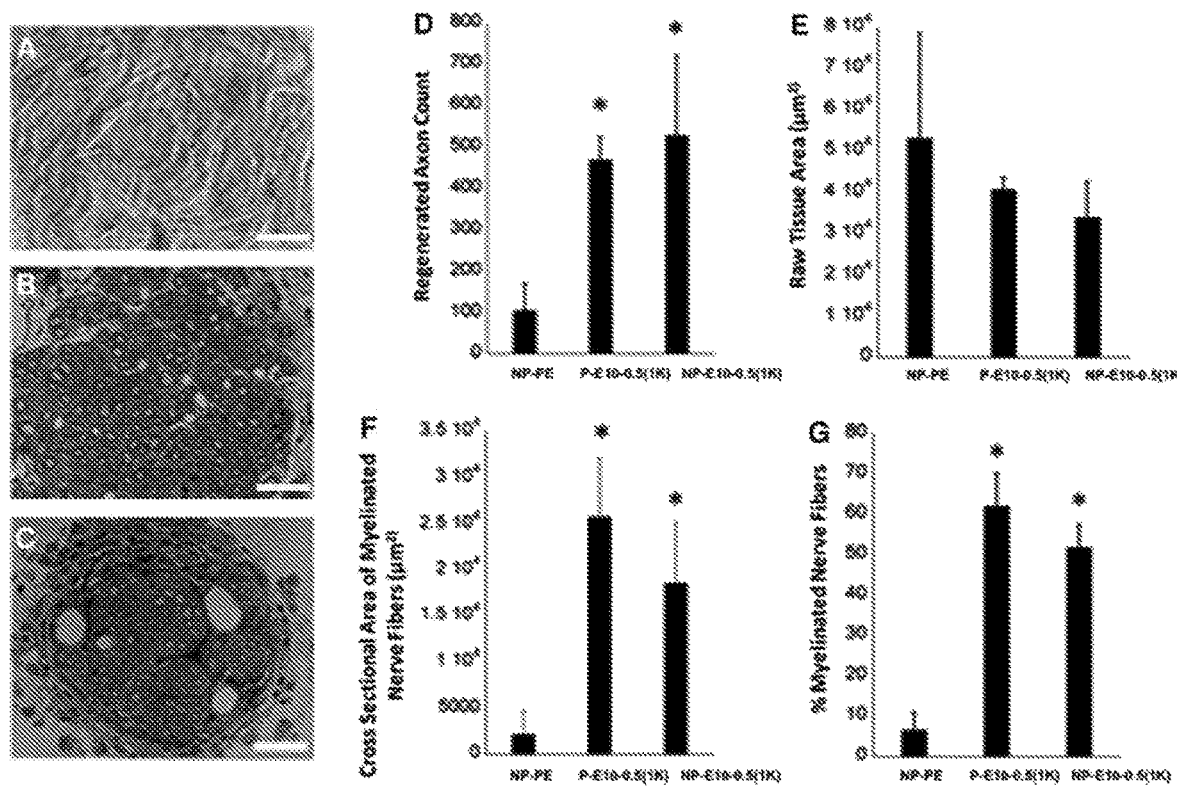

FIG. 6. Histomorphometric analysis of femoral nerves regenerated in E10-0.5(1K) and NP-PE conduits. (A–C) Representative cross-sectional images (40 x, Scale bar: 50 μm) of nerve sections stained with toluidine blue from the midpoint of regenerated femoral nerve after tubulization with either (A) nonporous PE conduits (NP-PE), (B) porous E10-0.5(1K) conduits [P-E10-0.5(1K)], or (C) nonporous E10-0.5(1K) conduits [NP-E10-0.5(1K)]. (D) Axon count of myelinated axons in the regeneration cable in the mid-conduit nerve section for each conduit type. (E) Raw tissue area. (F) Cross-sectional area of regenerated nerve fibers. (G)% myelinated nerve fibers in regenerating nerve cable. *Significant difference between group mean values from NP-PE ($p < 0.05$, one-way analysis of variance with Tukey's post hoc test).

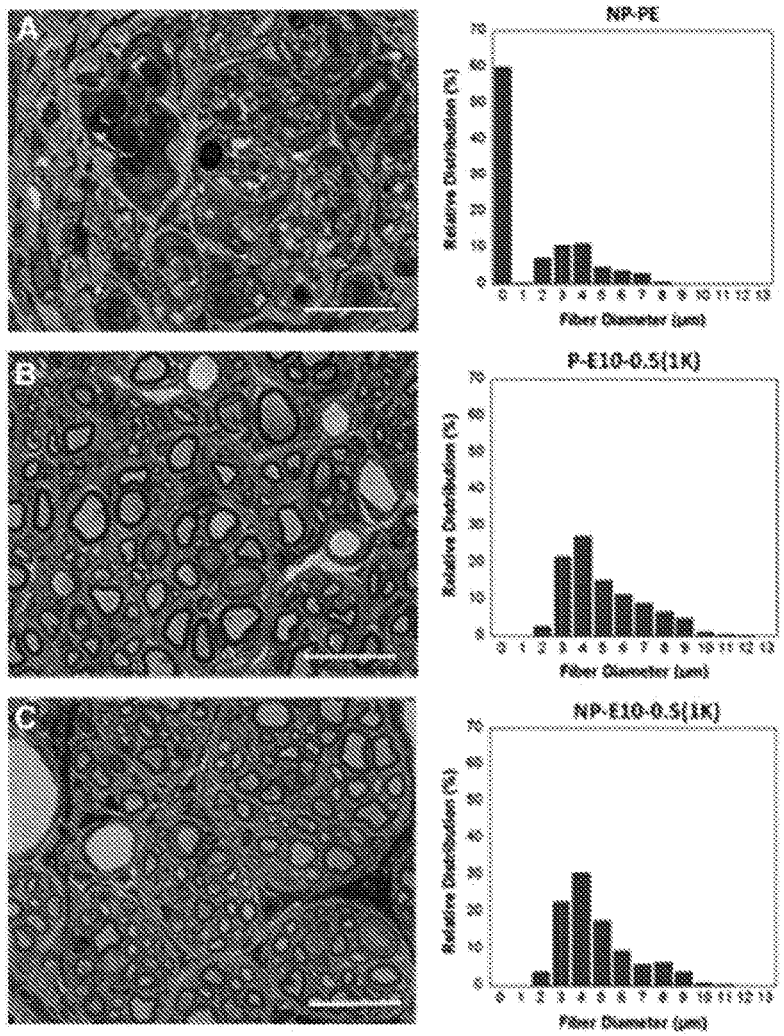

FIG. 7. Representative nerve sections and fiber diameter analysis. Representative crosssectional images (100x, Scale: 20 mm) of nerve sections stained with toluidine blue from the midpoint of regenerated femoral nerve and histogram of the relative distribution of nerve fiber diameter after tubulization with either (A) nonporous PE conduits (NP-PE), (B) porous E10-0.5(1K) conduits [P-E10-0.5(1K)], or (C) nonporous E10-0.5(1K) conduits [NP-E10-0.5(1K)]. Histograms of fiber diameters reveal a reduced number of small axons and an increased number of larger axons in animals treated with E10-0.5(1K) conduits as compared to animals treated with NP-PE conduits. There was a statistically higher relative distribution (%) of fiber diameters measuring 4, 5, 6, 7, and 8 mm in P-E10-0.5(1K) and NP-E10- 0.5(1K) conduits as compared to NP-PE conduits. ($p < 0.05$, one-way analysis of variance with Tukey's post hoc test).

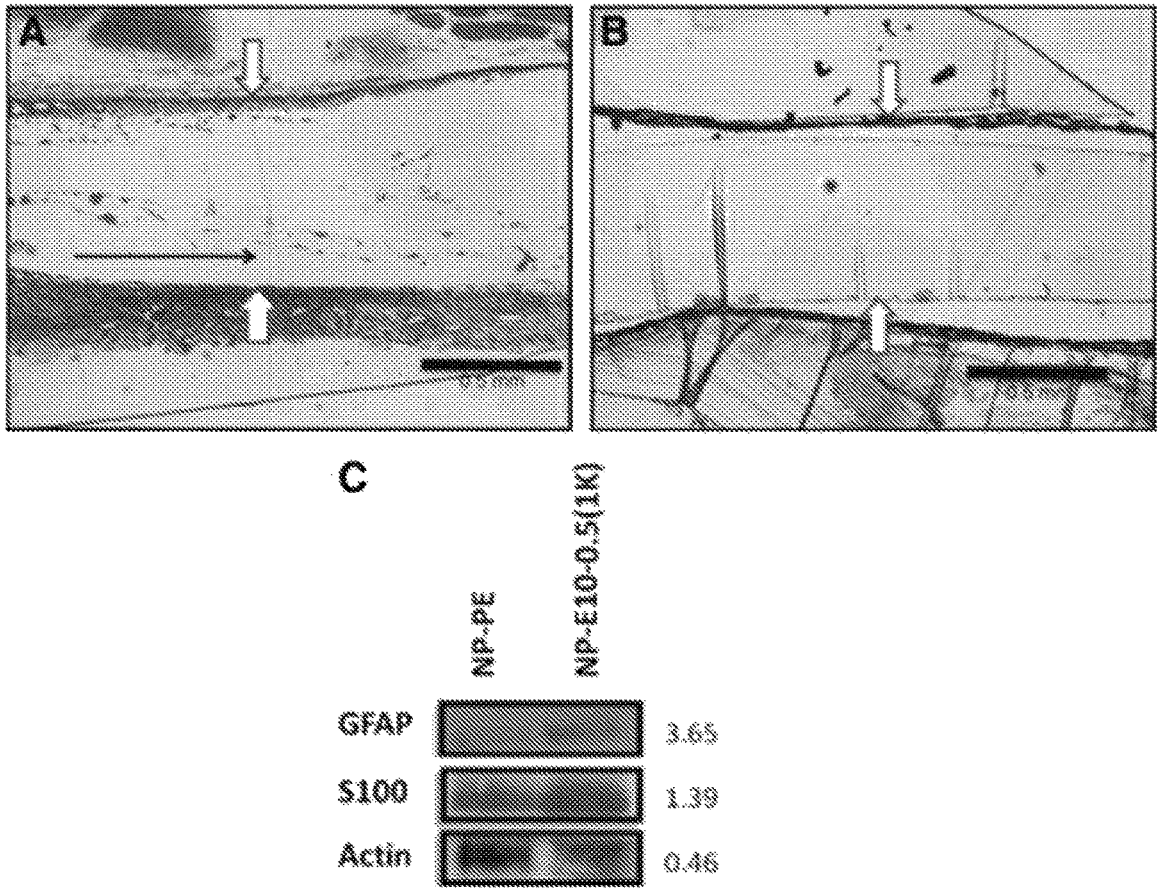

FIG. 8. Early differences in nerve repair between conduit materials. (A) and (B) show representative images of longitudinal sections of the acellular fibrin matrix within conduits at 2 weeks after implantation. (A) The natural matrix found in E10-0.5(1K) conduits. (B) The matrix present in NP-PE conduits. The polymers comprising the natural fibrin matrix in the E10-0.5(1K) had a predominant longitudinal orientation (black arrow in A), whereas no fibrin strands were observed in NPPE conduits. White arrows mark edges of the inner lumen within each conduit type. Scale bar: 0.5mm. (C) Representative western blot analysis of S100b and glial fibrillary acidic protein (GFAP) collected from nonporous E10-0.5(1K) and NP-PE conduit exudates 1 week after implantation. Values to the right of bands indicate relative optical densities of bands (NP-E10-0.5(1K)/NPPE).

BIOCOMPATIBLE IMPLANTS FOR NERVE RE-GENERATION AND METHODS OF USE THEREOF

CROSS-REFERENCE TO RELATED APPLICATIONS

This application claims the benefit priority of U.S. Provisional Application No. 62/148,087, filed on Apr. 15, 2015, the entire disclosure of which is incorporated herein by reference.

STATEMENT REGARDING FEDERALLY SPONSORED RESEARCH

This research was sponsored in whole or in part by the Armed Forces Institute of Regenerative Medicine award number W81XWH-08-2-0034. This work was also supported by the Center for Military Biomaterials Research (CeMBR) award number W81XWH-04-2-0031, the New Jersey Center for Biomaterials at Rutgers University and National Institutes of Health award R01NS078385. The U.S. Government has certain rights in the invention.

TECHNICAL FIELD

This patent document relates to the field of implants for nerve re-generation, and more particularly to biocompatible and bioresorbable nerve conduits and nerve wraps for the treatment or repair of a peripheral nerve injury whose biological performance is further enhanced with coatings to control the infiltration of fibrous tissue.

BACKGROUND

Peripheral nerve injury caused by trauma or surgery can lead to the loss of sensation and movement. The rate and extent of recovery is slow, usually incomplete and variable. The resulting loss of function can be very distressing to the patient and can lead to permanent disability due to the lack of adequate treatment options.

Nerve conduits are used for lesions of the peripheral nervous system in order to link the ends of severed nerves and to bridge the gap between the two ends. Nerve conduits provide the nerve fibers (axons) space to grow, protect the fragile newly grown nerve fibers from additional trauma, and ideally also provide protection against penetration by scar-forming, connective tissue cells (fibroblasts), which tend to obstruct axon growth. Nerve wraps are sheets that are wrapped around a damaged nerve to provide mechanical support, to minimize additional trauma to the damaged nerve, and to enhance functional recovery of the damaged nerve. Nerve conduits and nerve wraps are referred to in this patent document collectively as Nerve Assist Devices (NADs) unless it is necessary to specifically refer to nerve conduits or nerve wraps.

Degradable and resorbable NADs are preferred for nerve re-generation, since during healing and after the nerve fibers have been restored, the NAD breaks down and is resorbed so that the foreign structure does not require removal and does not risk damaging or irritating the regenerated nerve after the healing phase. NADs have been developed from synthetic polymers (for example, poly(lactic acid)), polymers derived from biological origin (for example, collagen, cross-linked gelatin), and human or animal cadaver-derived materials such as vein grafts and nerve grafts. However, many of these conduits are associated with poor healing resulting from swelling and reduction of luminal volume, suture pull-out, collapse, kinking, compression, and lack of mechanical strength to withstand the traction of moving joints.

A need remains for biocompatible and bioresorbable NADs in the form of nerve conduits and nerve wraps that not only offer desirable physical and mechanical properties, in particular kink-resistance and suturability, but also facilitate nerve fiber growth and provide protection against non-nerve tissue infiltration. Such NADs must also have suitable biodegradation and bioresorption profiles so that the timing of their loss of strength and physical integrity is matched with the time required for functional recovery of the damaged or severed nerve.

SUMMARY OF THE INVENTION

Various embodiments provide NADs suitable for the treatment or repair of peripheral nerve injury, offering significant improvements over conventional conduits in several aspects. First, the polymer used for constructing the nerve conduit is not only biocompatible, and bioresorbable, but has been found to support axon growth through the adsorption of endogenous proteins. Second, a library of polymers has been identified such that the optimal rate of degradation and bioresorption of the NAD can be adjusted to match the time required by the growing axons to traverse the length of the nerve gap that needs to be bridged. This adjustment of the rate of biodegradation and bioresorption can be made with only minimal effect on the polymer's mechanical and biological properties. Third, while braiding is well known, it has now been recognized that braiding offers important advantages when constructing NADs (improved compressive strength, improved resistance to kinking and stretching). Forth, the role of porosity of the NAD wall has been a hotly debated controversy in the scientific literature. It has now been recognized that the NAD wall must be porous to allow for nutrient exchange along the entire length of the device, but the porosity must be tightly controlled to prevent the undesirable infiltration of fibrous tissue into the inner lumen of the NAD. Thus, a forth aspect of this invention is the development of a hydrogel-like coating that controls the infiltration of fibrous tissue while still providing for improved oxygen and nutrient diffusion through the walls of the NAD. The combination of all four aspects results in a new and improved design for NADs such that the overall performance of the NAD leads to better functional nerve regeneration for the patient.

In an aspect of the invention there is provided a nerve conduit including a porous braided tube for nerve re-generation. The porous braided tube is coated with a bioresorbable hydrogel and fabricated from a resorbable, biocompatible polymer that supports axon growth due to the adsorption of endogenous proteins at its surface. The fibers are braided with pores in the range from 5 to 200 micrometers using a kink-resistant braiding pattern and the hydrogel coating material and thickness are selected to control the overall porosity such that nutrients and oxygen can diffuse through said hydrogel coating but the infiltration of fibrous tissue through the coating is prevented. In one embodiment, the resorbable biocompatible polymer has repeating units of the structure of Formula I:

Formula I

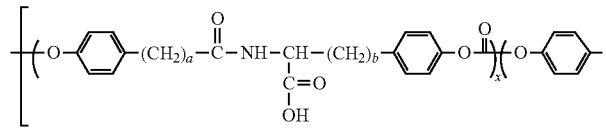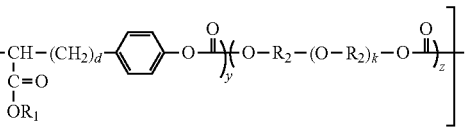

wherein a and b are independently 0 or an integer between 1 and 6, inclusive; wherein c and d are independently 0 or an integer between 1 and 6, inclusive; wherein each $R_1$ is independently selected from the group consisting of straight and branched alkyl groups containing up to 18 carbon atoms; wherein each $R_2$ is independently an alkylene group containing up to 6 carbon atoms; wherein k is between about 20 and about 200; and wherein x ranges between about 0.002 and about 0.20; z ranges between about 0.005 and 0.1; and x+y+z=1.00

In some embodiments of Formula I, a and b are two and one, respectively.

In some embodiments of Formula I, c and d are two and one, respectively, and $R_1$ is ethyl.

In some embodiments of Formula I, $R_2$ is ethylene and k is between about 25 and about 50.

In some embodiments, the NAD is fabricated by braiding. In preferred embodiments, the NAD is made by braiding fibers made of a polymer having repeating units of the above described Formula I.

In some embodiments, the NAD is fabricated using a helically wound biaxial braiding pattern.

In some embodiments, the porous NAD is coated with a bioresorbable hydrogel, which is cross-linked hyaluronic acid (HA).

In some embodiments, the bioresorbable HA hydrogel is cross-linked with poly(ethylene glycol) diacrylate) (PEGDA).

In some embodiments, the biocompatible nerve conduit further includes a second bioresorbable hydrogel for filling the interior lumen of the biocompatible nerve conduit.

In some embodiments, the second bioresorbable hydrogel for filling the interior lumen of the biocompatible nerve conduit is a collagen-based gel enhanced with a covalently attached neurotrophic factor such as the neurite-promoting peptide mimic of the Human Natural Killer-1 glycan (referred to as m-HNK-1).

In another aspect of the invention there is provided a method for the treatment or repair of a peripheral nerve injury using the implantation of the above described NADs, either in the form of a nerve conduit or in the form of a nerve wrap. The injured nerve's proximal and distal stumps are cleanly and perpendicularly sectioned so that no non-viable tissue remains. The conduit is then placed in situ so that about 1 mm of each stump can be fitted into the proximal and distal ends of the conduit respectively, and the nerve stumps are then secured to the conduit using conventional microneurosurgical techniques. The conduit may be further stabilized to the surrounding soft-tissue with sutures, or by flooding the repair site with a fibrin-like adhesive, or both. In the case of a nerve wrap, the damaged nerve is carefully placed within the wrap which is then closed around the damaged nerve by suturing the nerve wrap closed.

In yet another aspect of the invention there is provided the above described conduit with a nerve or nerve tissue or nerve cellular component that is inserted into the interior lumen of the biocompatible nerve conduit. Cellular components may be injected within a hydrogel to fill the lumen, or may be injected into a hydrogel-type filler within the lumen. Tissue components may be laid into the lumen after the conduit is slit longitudinally to provide access. Alternatively, a nerve wrap can be used to enclose the damaged nerve and any of the above described fillers, followed by closing the conduit or wrap by suturing. As part of this aspect of the invention, it is possible to create conduits and wraps that have an inherent tendency to retain a curled-up shape, facilitating the closure of the device by suturing after the damaged nerve and filler materials have been successfully placed within the inner lumen of the device.

In some embodiments, the second bioresorbable hydrogel for filling the interior lumen of the biocompatible NAD is a collagen-derived hydrogel enhanced with a covalently attached axon-promoting peptide mimic of poly(sialic acid) (referred here as mPSA).

In some embodiments, the interior lumen of the biocompatible nerve conduit is a hydrogel that contains a therapeutic dose of, and is capable of releasing any of the known axon growth enhancing biological factors, such as m-HNK-1, m-PSA, or others.

In yet another aspect of the invention, the same polymers are fabricated into braided sheets that can optionally be coated with the same hydrogels, containing optionally the same biologically active substances (m-HNK-1, m-PSA, or other small molecule mimics of known nerve fiber growth enhancing biological factors) so that the sheets can be used as nerve wraps rather than as nerve conduits.

In yet another embodiment of the invention, the addition of a 5-HT$_4$ agonist, including, but not limited to, BIMU-8, Cisapride, CJ-033,466, Mosapride, Prucalopride, Renzapride, RS-67333, SL65.0155, Zacopride and Tegaserod, were found to further support the growth of axons within the lumen of a NAD.

BRIEF DESCRIPTION OF THE DRAWINGS

FIG. 1 shows a polymer unit consisting of desaminotyrosyl tyrosine ethyl ester (DTE) copolymerized with 10 mol % desaminotyrosyl tyrosine (DT), and 0.50 mol % poly (ethylene glycol) (PEG) (MW 1000).

FIG. 2 shows cross-section views of conduits with different porosity.

FIG. 3 shows in vitro evaluation of neurite outgrowth and Schwann cell proliferation and extension on two-dimensional (2D) films of the polymer of FIG. 1 and polyethylene (PE) in comparison with control substrates, tissue culture polystyrene (TCPS), and glass.

FIG. 4 shows relative absorption of neurosupportive extracellular matrix (ECM) proteins (laminin, fibronectin, and collagen type I) on 2D films of the polymer of FIG. 1 and PE in comparison with a control substrate.

FIG. 5 shows histomorphometric analysis of femoral nerves regenerated in the polymer of FIG. 1 and non-porous polyethylene (NP-PE) conduits.

FIG. 6 shows video frames of the functional measurements performed on mice following implantation of the conduit and metrics of functional recovery promoted by the polymer of FIG. 1 and non-porous polyethylene conduits in vivo.

FIG. 7 shows representative nerve sections and fiber diameter analysis.

FIG. 8 shows early differences in nerve repair between conduit materials.

DETAILED DESCRIPTION

Various embodiments provide nerve conduits for nerve re-generation. Conduits fabricated with polymers of the present invention in suitable forms offer potential advantages including suitable ranges of biodegradation and resorption rates, desirable mechanical properties, and compatibility with the surrounding tissue. Coatings on the porous fiber tube of such conduits further promote axon growth and serves as a barrier against non-nerve tissue. Hydrogel luminal fillers also facilitate a faster axonal regeneration as compared to fibrotic tissue infiltration. Conduits of the present invention may also include a pre-implanted nerve or nerve tissue as a seed, promoter, or bridge for nerve regeneration. The devices of the invention thus find utility in the treatment of a trauma or an injury to a nerve or nerves in the body of a human or an animal.

Throughout this patent document, various publications are referenced. The disclosure of these publications in their entirety is hereby incorporated by reference into this application in order to more fully describe the state of the art to which the disclosed matter pertains. While the following text may reference or exemplify specific polymers, fiber tubes, or nerve conduits, it is not intended to limit the scope of the invention to such particular references or examples. Various modifications may be made by those skilled in the art, in view of practical and economic considerations. In order to more clearly and concisely describe the subject matter of the claims, the following definitions are intended to provide guidance as to the meaning of terms used herein.

Definition

The articles "a" and "an" as used herein refers to "one or more" or "at least one," unless otherwise indicated. That is, reference to any element of the present invention by the indefinite article "a" or "an" does not exclude the possibility that more than one of the elements is present.

"About" as used herein refers to the referenced numeric indication plus or minus 10% of that referenced numeric indication.

The terms "alkyl", "alkylene" and similar terms have the usual meaning known to those skilled in the art and thus may be used to refer to straight or branched hydro-carbon chain fully saturated (no double or triple bonds) hydrocarbon groups. Terminal alkyl groups, e.g., of the general formula —$C_nH_{2n+1}$, may be referred to herein as "alkyl" groups, whereas linking alkyl groups, e.g., of the general formula —$(CH_2)_n$—, may be referred to herein as "alkylene" groups. The alkyl group may have 1 to 18 carbon atoms (whenever it appears herein, a numerical range such as "1 to 18" refers to each integer in the given range; e.g., "1 to 18 carbon atoms" means that the alkyl group may consist of 1 carbon atom, 2 carbon atoms, 3 carbon atoms, etc., up to and including 18 carbon atoms, although the present definition also covers the occurrence of the term "alkyl" where no numerical range is designated). The alkyl group may also be a medium size alkyl having 1 to 6 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The term "degradation" or "biodegradation" as used herein refers to the process leading to the chemical cleavage of the polymer backbone, resulting in a reduction in polymer molecular weight and mechanical strength. The rate of polymer degradation under physiological conditions is predominantly determined by the type of bonds used to link the individual polymer repeat units together. Hence, polyanhydrides, e.g., polymers containing the highly labile anhydride linkage, will tend to degrade faster than polyesters. In contrast, the term "resorption" or "bioresorption" is defined as the process leading to a reduction of the mass of an implanted device. The rate of resorption is predominantly governed by the solubility of the polymer itself or its degradation products. The resorption of an implant is complete, once the entire mass of the implant has been removed from the implant site.

The term "biocompatible" has many different meanings in the scientific literature. In the context of this patent document, a biocompatible implant is understood to function within the human body without causing a clinically unacceptable tissue response at the implant site, where an unacceptable tissue response would, under reasonable and established clinical practice, require the removal of the implant from the human body.

In one aspect there is provided a biocompatible nerve conduit for nerve re-generation including a porous fiber tube coated with a bioresorbable hydrogel. The nerve conduits of the present invention are fabricated from fibers that offer advantages over conventional conduits in terms of biodegradation and bioresorption profile, mechanical properties, protein adsorption, fibrin matrix formation, and Schwann cell infiltration. Results from in vitro and in vivo study (FIGS. 1-8) indicate that a nerve conduit incorporating the four design strategies described above performs significantly better than conventional conduits that do not incorporate those design strategies. Specifically, the conduit of the present invention was compared with a conventional conduit constructed with polyethylene (PE). The four design strategies described above are (1) a polymer composition that supports axon growth, (2) use of a polymer library so that that the rate of degradation and bioresorption of the NAD can be adjusted to the time required by the growing axons to traverse the length of the nerve gap, (3) a braided structure, (4) a coating that controls porosity for optimal nutrient transport without allowing infiltration of fibrous tissue. It has now been found that this combination of design strategies imparts a significant performance advantage that can lead to better clinical outcomes for the patient in need of peripheral nerve regeneration.

In some embodiments, the polymer fiber material is composed of desaminotyrosyl-tyrosine alkyl ester (DTE), desamniotyrosyl-tyrosine pendant free carboxylic acid (DT), and poly(ethylene glycol) (PEG). The molar fraction of free carboxylic acid units and PEG units in the polymer described herein can be adjusted to modify the mechanical properties and degradation rates of NADs made from such polymers. For example, polymers with lower amounts of free carboxylic acid will tend to have longer lifetimes in the body. Further, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are desirable or required.

In one embodiment, the fiber material is composed of a biocompatible polymer having repeating units of the structure (Formula I):

DT, between about 2 and about 20 mol %, and preferably between about 5 and about 20 mol %.

Poly(alkylene glycol) segments, such as PEG, decrease the surface adhesion of the poly-mers. By varying the molar fraction of poly(alkylene glycol) segments in the block copolymers provided by the present invention, the hydrophilic/hydrophobic ratios of the polymers can be changed to adjust the ability of the polymer coatings to modify cellular behavior. Increasing levels of poly(alkylene glycol) inhibit cellular attachment, migration and proliferation. Secondarily, PEG increases the water uptake, and thus increases the rate of degradation of the polymer. Accordingly, in an embodiment, polymers are selected in which the amount of poly(alkylene glycol) is limited to between 0.5 and about 10 mol %, and preferably between about 0.5 and about 5 mol %, and more preferably between about 0.5 and about 1 mol %. The poly(alkylene glycol) may have a molecular weight of 1 k to 2 k.

Formula I

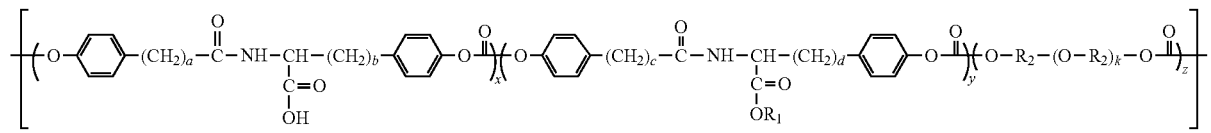

wherein a and b are independently 0 or an integer between 1 and 6, inclusive; wherein c and d are independently 0 or an integer between 1 and 6, inclusive; wherein each $R_1$ is independently selected from the group consisting of straight and branched alkyl groups containing up to 18 carbon atoms; wherein each $R_2$ is independently an alkylene group containing up to 6 carbon atoms; wherein k is between about 20 and about 200; and wherein x ranges between about 0.02 and about 0.20; z ranges between about 0.005 and 0.10; and x+y+z=1.00

In some embodiments, a and b are two and one, respectively.

In some embodiments, c and d are two and one, respectively, and $R_1$ is ethyl.

In some embodiments, R2 for said polymer is ethylene and k is between about 25 and about 50.

The synthesis of various polycarbonate polymers is generally known in the art, includ-ing for example, the methods disclosed in U.S. Pat. Nos. 6,120,491 and 6,475,477, the disclosures of which are incorporated herein by reference. Polymers having pendent free carboxylic acid groups are preferably prepared from the corresponding benzyl and tert-butyl ester polymers to avoid cross-reaction of the free carboxylic acid group with co-monomers. The benzyl ester polymers may be converted to the corresponding free carboxylic acid polymers by the palladium catalyzed hydrogenolysis method disclosed in U.S. Pat. No. 6,120,491. The tert-butyl ester polymers may be converted to the corresponding free carboxylic acid polymers through the selective removal of the tert-butyl groups by the acidolysis method disclosed in U.S. Patent Publication No. 20060034769, also incorporated herein by reference.

In some embodiments, polymers are selected which degrade or resorb within a predetermined time. For this reason, embodiments according to the present invention include polymers with molar fractions of monomeric repeating units with pendant fee carboxylic acid groups, such as In some embodiments, polymers are selected having intrinsic physical properties appropriate for use in nerve conduits with suitable mechanical properties including elasticity, rigidity, strength and degradation behavior. Such polymers include, if the polymer is amorphous, polymers with a glass transition temperature greater than 37° C. when fully hydrated under physiological conditions and, if the polymer is crystalline, a crystalline melting temperature greater than 37° C. when fully hydrated under physiological conditions.

It is to be understood that other biocompatible degradable polymers can be used to form fibers that provide or reinforce certain desirable properties of the resulting nerve conduits. Examples of other polymers that may be used include, but are not limited to, poly(lactic acid), poly(glycolic acid), poly(lactic-co-glycolic acid), polycaprolactone, various poly(amino acid)s and polyanhydrides. Other natural or non-natural fiber materials, for example, collagen, cellulose, chitosan, and their derivatives, may alternatively or additionally be utilized to provide or reinforce certain desirable properties of the resulting nerve conduits (see, for example, U.S. Pat. No. 8,216,602).

In some embodiments, the biocompatible polymer composition is biodegradable and bioresorbable. The NAD of the present invention is preferably biodegradable and bioresorbable, and has a specific degradation profile that may be tuned depending on the length of the nerve gap that needs to be restored. Nerve fibers grow approximately 1 mm per day, or about 1 inch per month. Hence for the successful regeneration of a 2 inch nerve gap, the healing process will require at least 2 months and the NAD should retain much of its mechanical strength for at least 2 months. For the regeneration of a 4 inch nerve gap, the NAD should retain much of its mechanical strength for at least 4 months to ensure complete recovery before the NAD becomes mechanically too weak to support the regrowth of the injured nerve fibers. In some embodiments, the degradation profile may be controlled by forming the NAD from multiple polymer fibers, each having a different degradation profile.

In some embodiments the polymer composition is radiopaque, whereas in other embodiments it is not radiopaque. In some embodiments, the polymers are iodinated on one or more aromatic rings of the polymeric units (see, for example, U.S. Pat. No. 6,475,477). Such modification allows for detecting and tracking of the NADs with medical imaging techniques.

In some embodiments, the NAD may have a shape memory.

FIG. 1 illustrates a polymer fiber material composed of 89.5 mol % desaminotyrosyl tyrosine ethyl ester (DTE), 10 mol % desaminotyrosyl tyrosine (DT), and 0.5 mol % poly(ethylene glycol) (PEG, molecular weight [Mw]=1 kDa) [designated as E10-0.5(1K)]. Longer axons were observed on this polymer when compared to PE (FIG. 2), as indicated by the peak shift to the right of the PE and control substrate peaks. An assessment of Schwann cell attachment and extension of processes on the differing substrates revealed that this polymer similarly promoted these aspects as compared to PE (FIG. 2B, C). The adsorption of proteins essential to nerve regeneration to the different materials was also significantly different (FIG. 3). The amounts of three ECM proteins adsorbing to this polymer were significantly greater as compared to PE films as shown in FIG. 4.

In motor function recovery study, animals that received 89.5 mol % DTE-10 mol % DT-0.5 mol % PEG1K polymer conduits showed marked improvement in Foot Base Angle (FBA) compared to mice that received NP-PE conduits. A significantly greater number of axons were present within regenerating nerve cables formed within conduits of this polymer with a smaller area of raw fibrous tissue, regardless of the presence of pores in the outer walls (FIG. 5). The cross-sectional area of myelin-ated nerve fibers was significantly greater in all conduits as compared to the NP-PE conduit, and a greater percentage of this area was occupied by myelinated nerve fibers. The conduits of the present invention generated nerve cables with a large number of axons, fascicular structures, a large range of nerve fiber diameters and little fibrous tissue, while the NP-PE conduits contained few, if any, evident axons (FIG. 7). The inner lumina were completely filled with what appeared to be dense, fibrous tissue. Longitudinal sections demonstrate that the fibrin matrix develops within the conduits of the present invention earlier than within the NP-PE (FIG. 8).

The porous NADs of the present invention can be fabricated using a braiding process. Numerous variations of the braiding process are known to those skilled in the art. By making changes in the braiding pattern, the overall mechanical properties of the resulting NADs can be tuned to address different medical needs. A common braiding pattern that was found useful for creating kink-resistant nerve conduits is referred to as a helically wound biaxial braid. In addition, multiple, different types of fibers can be used in combination to create a braided device comprised of different polymers. Using only those polymers having repeating units of Formula I, a multifilament device can be constructed in which the individual fibers differ in their degradation rate. This approach can be used to fine-tune the degradation and resorption profile of the device. In another embodiment, suitable drugs can be incorporated into individual polymer fibers. By using combinations of fibers, each loaded with a different drug, a wide range of pharmaceutically enhanced NADs can be envisioned, each releasing a customized mixture of different drugs to assist in nerve regeneration in a "personalized medicine" approach. The concept of using different fibers to braid a NAD is a powerful means to optimize the overall performance characteristics of the device and provides a heretofore unrecognized degree of flexibility in device design. An additional potential application for the use of multiple, different fibers to create a braided NAD is to combine fibers derived from biopolymers (collagen, gelatin, crosslinked alginate and others) with fibers from synthetic polymers such as the tyrosine-derived polycarbonates described above. In the braiding process, individual fibers are laid over each other thereby creating a unique hybrid structure whose properties can be fine tuned by the choice of individual fibers, their relative proportion within the braided construct and the braiding pattern used. Procedures for constructing tubes using braiding well known in the art (see for example U.S. Pat. No. 8,106,014).

The porous NADs are constructed by braiding. As illustrated in figures and examples of this patent document, braided conduits offer advantages in terms of physical and mechanical properties, but significant overall performance enhancement is only obtained when braiding is combined with the other critical design strategies described above (polymer compositions that enhance neurite growth, use of polymer libraries to tune degradation profile, and a porosity-controlling coating). These design strategies have synergistic effects that have not previously been recognized and that lead to the observed enhanced nerve re-regeneration.

Braided conduits can provide desirable mechanical properties including flexibility and kink resistance and tensile strength, which are important criteria in conduit design, especially for large nerve gaps in areas of high mobility. To avoid pinching or re-severing the fragile regenerating nerve, conduits must be able to bend without experiencing luminal occlusion. Braided conduits of the present invention demonstrate such capacity in a kink test, where conduits are bent on a wire until a kink (reduction of the lumen inner diameter) occurs. Studies on braided conduits (fabricated from poly(DTE carbonate), abbreviated E0000) show that in comparison with clinically used NeuraGen® conduits (fabricated from collagen I, Li et al., Clin Mater 1992; 9(3-4): 195-200.) and non-porous dipcoated conduit (fabricated from poly(DTE carbonate), braided conduits (fabricated from poly(DTE carbonate)) resisted kinking and maintained constant lumen diameter when bent at angles exceeding 125°. Braided conduits also resumed their original shape after release of the load, whereas dipcoated and NeuraGen® conduits partially or completely occluded the lumen when bent and did not resume their original shape. In addition, poly(DTE carbonate) braided conduits are able to withstand tensile, compressive and shear forces created by limb movement and muscular contraction.

Studies also show that the NADs of the present invention are well-tolerated and do not elicit strong inflammatory host response. The formation of fibrous capsules around the implanted NADs of the present invention is within acceptable limits indicating a minimal inflammatory host response.

The NADs of the present invention have a tightly controlled level of porosity. The size of pores within the braided material must be in a range suitable for promoting effective nutrient and oxygen exchange along the entire length of the device while also acting as a barrier against scar tissue infiltration. The pore size of the NADs can be manipulated by using different braiding processes, and/or by controlling the fiber diameter. Then, the overall porosity can be further manipulated by the hydrogel coating process. In exemplary embodiments, braided conduits are fabricated by first generating small diameter fibers that are either used individually or twisted together to form yarns, and are loaded onto a braiding apparatus. The apparatus wraps the fibers or yarns around a mandrel to generate the conduit. Fibers or yarns can be braided around the mandrel in a variety of braiding patterns. The diameter of the mandrel determines the lumen diameter and the fiber or yarn diameter determines the thickness of the conduit walls. Once suitable fibers are available, braided conduits can be rapidly and reproducibly fabricated without dimensional limitations.

Hydrogel coatings can be used to further fine-tune the overall porosity of the NAD. Non-limiting examples of pore sizes resulting from the coating process are about 3-40 µm. Without hydrogel coating, these braiding-induced pores are too large and would allow the undesirable infiltration of fibrous tissue into the lumen of the NAD. The lack of control over the pore size by previously known braided nerve conduits is one of the reasons for their failure to lead to clinically useful nerve regeneration. The hydrogel coating process of the present invention has addressed this inherent disadvantage of the braiding process. Various known techniques including dip-coating can be applied in coating the NADs of the present invention.

Various hydrogels from natural sources or synthetic origin, including for example polypeptide-based hydrogels, polysaccharide-based hydrogels, and petrochemical-based hydrogels, can be used individually or in combination with each other for coating the braided NADs. Non-limiting examples of coating material include alginic acid, hyaluronic acid, and poly(acrylic acid) hydrogel.

In some embodiments, the hydrogel for coating the fibrous tube is further functionalized by a cross-linking agent. This is important whenever the non-crosslinked hydrogel would be water soluble or would be too weak to provide a mechanically stable coating. Non-limiting examples of crossing-linking agents include poly(ethylene glycol diacrylate (PEGDA), poly(ethyelene glycol diglycidyl ether), 1-ethyl-3-(3-dimethylaminopropyl) carbodiimide, and divinyl sulfone. The amount of hydrogel and the extent of cross-linking required to create an effective coating depend on various factors including the initial pore size of the braided NAD, the diameter and length of the tube, the size and level of porosity, and possibly also on the specific nerve to be regenerated. Methods of cross-linking hydrogels are readily available in the literature and can be practiced without undue experimentation (see for example, Nilimanka, International Journal of Pharmacy and Pharmaceutical Sciences, 2013, 5(4), 55-58; Hennink et al., Adv. Drug Deliv. Rev. 2002 Jan. 17; 54(1):13-36). In some embodiments, the bioresorbable hydrogel for coating the NADs is cross-linked hyaluronic acid (HA). In some embodiments, the cross-lining agent is PEGDA.

Hydrogel coating of porous tubes can lead to significantly improved nerve regeneration comparing with non-coated porous tubes. Studies on conduits fabricated from E1001(1 k) (a copolymer consisting of 89 mol % desaminotyrosyl-tyrosine ethyl ester (DTE), 10 mole percent desaminotyrosyl-tyrosine (DT) and 1 mol % poly(ethylene glycol)) demonstrates the effect of hydrogel coating on nerve regeneration. Out of four types of conduits (uncoated, cross-linked hyaluronic acid (HA) coating, electronspun 89 mol % DTE-10 mol % DT-1 mol % PEG 1K polymer fiber coating, and a combination of electronspun 89 mol % DTE-10 mol % DT-1 mol % PEG 1K polymer coating subsequently coated with HA), the HA-coated conduits all showed significantly better results in nerve re-generation. Uncoated braided conduits showed many regenerated axons within fascicles that were loosely organized and a considerable amount of non-nerve tissue. Electrospun coated braided conduits also showed inconsistent axon growth with non-nerve tissue, suggesting that the electrospun mat surrounding the braided conduit may have facilitated fibrous tissue infiltration.

By contrast, HA-coated conduits all showed rounded and densely packed nerve cables with tightly packed fascicles and axons. These features were not replicated in the nerves regenerated within braided conduits coated with both electrospun fibers and HA where extensive fibrous tissue was observed that had intercalated within the regenerating nerve axons and fascicles. In addition, the tibialis anterior (TA) muscle weight recovery for the HA-coated braided conduits was significantly higher than for the uncoated conduits. Further, electrophysiological measurements of nerve conduction through the defect and to reinnervated muscle groups were used to assess the compound muscle action potential (CMAP). Among the conduit groups, HA-coated braided conduits had the highest CMAP amplitudes with approximately 14% of the CMAP signal recovered at the 16-week end-point.

In some embodiments, the nerve conduit is filled with a bioresorbable hydrogel in its interior lumen. The bioresorbable hydrogel facilitates the formation of a fibrin matrix which serves as a physical bridge across the nerve gap and provides a structure for cells to migrate across. Non-limiting examples of hydrogels as filler include hydrogels derived from laminin, alginate, collagen, hyaluronic acid, and their combination (see, for example, Verdú, et al. Restorative Neurology & Neuroscience 2002, 20: 169; Ceballos et al. Experimental Neurology 1999, 158: 290-300). In the case of long nerve gaps, porous tubes are often required because they allow for nutrient, oxygen, and waste exchange along the length of the conduit and even allow for infiltration of blood vessels. However, the porosity of the conduit also allows for infiltration of non-neuronal fibrous tissue. It is thus desirable that a hydrogel filler differentiate between neuronal tissue and non-neuronal fibrous tissue, facilitating a faster axonal regeneration as compared to fibrotic tissue infiltration.

Accordingly, in some embodiments, the hydrogel for filling the interior lumen of the tube is enhanced by a cell-signaling or neurite-promoting moiety, which favors axon growth and appropriate motor neuron targeting. Non-limiting examples for such neurite-promoting moiety includes a peptide mimetic of Human Natural Killer 1 glycan (m-HNK), brain-derived neurotrophic factor (BDNF), platelet-derived growth factor (PDGF), and glial growth factor (GGF). In some embodiments, the neurite-promoting moiety is a peptide mimetic of the Human Natural Killer 1 glycan (m-HNK). Procedures for attaching a neurite-promoting moiety to a hydrogel are well known in the art and can be practiced without undue experiments. For example, a m-HNK-enhanced collagen can be prepared by grafting peptide mimetic of the Human Natural Killer 1 (m-HNK) glycan onto the collagen using EDC chemistry as previously described (see, for example, Masand, et al. Biomaterials, 2012, 33: 8353-62).

In another aspect there is provided a method for the treatment or repair of a peripheral nerve injury comprising the implantation of the nerve conduit of the present invention. Protocols for implanting nerve conduits are readily available and can be practiced without undue experiments (see, for example, Rui et al. Acta Biomaterialia 2012; 8(2):511-518; de Ruiter et al., Exp Neurol 2008; 211(2): 339-50). In exemplary embodiments, the two ends of the nerve conduit are connected with the two nerve stumps formed at the lesion to bridge the gap existing between them.

The lumen of the nerve guide remaining between the nerve stumps specifies the direction for the regenerating axons and avoids any incorrectly-guided growth, thus promoting a targeted regeneration (see for example, U.S. Pat. No. 8,216, 602).

In another aspect there is provided a nerve conduit that is prefilled with tissue engineered (e.g., laboratory grown) axons. The prefilled axons facilitate the re-generation of nerve by serving as a seed that providing a bioactive support for tissue growth. The concept of using biologic components and/or living engineered nerve tissue to prefill the conduit prior to implantation into the body of a patient has great potential and may facilitate the healing of nerve gaps of unprecedented length. The use of issue engineered nerve grafts (TENGs) has been pioneered by the University of Pennsylvania and Axonia Medical (Kalamazoo, Mich.). For this revolutionary approach to reach its full clinical potential, the TENGs need to be enclosed within a carefully optimized NAD. Maintaining nutrient exchange, mechanical properties and kink resistance over large gaps while optimizing the prolonged period of bioresorption is a difficult challenge that has so far not been addressed satisfactorily by any of the currently available synthetic nerve conduits. Researchers at the University of Pennsylvania and Axonia have now shown that the NADs of the present invention support the ingress of Schwann cells and the extension of host axons along the TENGs, and result in improved rates of nerve regeneration as compared to autografts. The use of the NADs of the present invention prefilled with living (engineered) nerve tissue represents an additional embodiment of the present invention.

EXAMPLES

Example 1

Conduit Fabrication

E10-0.5(1K) (FIG. 1), composed of 89.5 mol % desaminotyrosyl tyrosine ethyl ester [DTE], 10 mol % desaminotyrosyl tyrosine [DT], and 0.5 mol % of poly(ethylene glycol) [PEG] with Mw of 1 kDa, was synthesized utilizing previously published procedures (Magno, et al., J Mater Chem 20, 8885, 2010). Hollow conduits with an inner diameter of 580 mm were fabricated using a dip-coating (KSV dip-coater; KSV Instruments, Inc.) technique in which a Teflon-coated mandrel was dipped at a constant rate (40 mm/min) into a polymer solution. For nonporous conduits, a solution containing 900 mg of polymer in 3 mL of methylene chloride was used. For porous conduits, a solution of 450 mg of sucrose crystals, sieved to 25-45 mm, and 450 mg of polymer dissolved in 3 mL of methylene chloride was used. Following dip coating, the mandrels were dried in vacuum overnight, and conduits were pulled off and cut to 5 mm length for in vivo evaluation. For porous conduits, the sucrose was leached out in water to create a porous structure. Commercially available PE tubes were also used as nerve conduits (5 mm length, 0.58 mm inner diameter; Becton Dickinson).

In Vitro Evaluations

In vitro assessment of conduit material with spinal cord neurons and Schwann cells was conducted. The effect of 89.5 mol % DTE-10 mol % DT-0.5 mol % PEG 1K polymer and polyethylene (PE) on neurite outgrowth and Schwann cell attachment and extension was determined using glass coverslips spin coated with 89.5 mol % DTE-10 mol % DT-0.5 mol % PEG 1K polymer (2.5% w/v solution in tetrahydrofuran) or coated with a thin self-adhering film of PE (VWR). To facilitate cell survival and outgrowth, coverslips were coated with 200 μg/mL of poly-L-lysine (PLL; Sigma) followed by 20 μg/mL of laminin (Invitrogen). Embryonic spinal cord neurons were isolated and purified for a motor rich population. Schwann cells were isolated and purified from the sciatic nerves of P2 neonates according to published protocols (Honkanen, et al., Eur J Neurosci 26, 953, 2007), yielding cultures with >95% of cells staining positive for S100β. Cells were seeded onto coverslips (1.5× $10^4$ cells/coverslip) and maintained for 48 h at 37° C. with 5% $CO_2$. Neurites and the process outgrowth of neurons and Schwann cells were evaluated using the β-tubulin antibody (Covance; 1:500) and S100β (Abcam; 1:500), respectively, with both cell types visualized using the Alexa Fluor 488 secondary antibody (Invitrogen). Nuclear staining was performed with Hoechst 33258 stain (AnaSpec, Inc.). The length of total neurites/processes per cell was measured using ImageJ (NIH). For each coverslip, 10 randomly chosen representative images were analyzed in a double-blind manner and neurites were binned based on their length.

Protein Adsorption Assay.

The relative amounts of protein adsorption for three extracellular matrix (ECM) molecules (laminin [Invitrogen], fibronectin [Invitrogen], and collagen type I [Advanced Biomatrix]) on 89.5 mol % DTE-10 mol % DT-0.5 mol % PEG 1K polymer and PE films were evaluated. 89.5 mol % DTE-10 mol % DT-0.5 mol % PEG 1K polymer films prepared by compression molding and PE films (VWR) were fit into a 96-well plate. A 70 mL solution of each protein (20 mg/mL in dd$H_2O$) was added to each well and allowed to adhere to the films at 37° C. for 48 h. After the supernatant was removed, each well was rinsed thoroughly and blocked with media containing fetal calf serum. After rinsing, the primary antibodies against each protein were added for 1 h at room temperature (Millipore; 1:100). The entire rinsing process was repeated, and a secondary horseradish peroxidase (HRP)-conjugated antibody (Millipore; 1:200 dilution) was added for 1 h at room temperature. The rinsing process was repeated once more, and Luminol (Invitrogen) was added to each well. After 5 min, the luminescence from each well was read using a Tecan plate reader with an integration time of 1000 ms and a settle time of 500 ms. Protein amounts were normalized to the control surface, tissue culture polystyrene.

In Vivo Evaluation.

Surgical methods and animal groups. All experiments were conducted in accordance with the Institutional Animal Care and Use Committee (IACUC). Female C57BL/6J mice (age 3 months) were anesthetized by intraperitoneal injection of a ketamine (80 mg/kg) and xylazine (12 mg/mg) mixture. The left femoral nerve was surgically exposed, and a nerve transection was performed at a distance ~3 mm proximal to the bifurcation of the nerve. The cut ends of the nerve were inserted into the saline-filled nerve conduit and fixed on each end with a 10-0 nylon suture (Ethicon), so that a 5 mm gap was present between the proximal and distal stump. The incised skin was closed with wound clips, which were removed 2 weeks post-surgery. Three animal groups (eight animals each) receiving the three conduit types were compared over a 15-week time period, including P-E10-0.5 (1K), NP-E10-0.5(1K), and NP-PE.

Motor Function Recovery.

Functional recovery was assessed using a single-frame motion analysis approach (SFMA). 40 Animals were trained to perform a beam walking test before implantation of the conduit. Following surgery, this test was performed weekly until the endpoint of the experiment. Rear view videos of the mice walking were collected using a high-speed camera (A602fc; Basler). The movements of the hind legs during the normal gait cycle were analyzed from individual video frames using Simi-Motion (SIMI Reality Motion Systems). The foot base angle (FBA)40 was measured to evaluate the function of the quadriceps muscle. Additionally, the protraction limb ratio (PLR)40 was measured, while the mouse performed a voluntary movement during a pencil grip test.

A recovery index (RI) was calculated for each animal for both the FBA and the PLR to provide a relative measure of functional recovery. The RI was calculated as a percentage using the following formula:

$$RI = \left[\frac{(X_{week\ y} - X_{week\ 1})}{(X_{week\ 0} - X_{week\ 1})}\right] \times 100,$$

where $X_{week\ 0}$, $X_{week\ 1}$, and $X_{week\ y}$ are intact values at week 0 (either FBA or PLR), values measured at week 1 after injury, and at week y (where y is the endpoint of the study, week 15), respectively (Irintchev, et al., Eur J Neurosci 22, 802, 2005). An RI value of 100 indicates complete recovery of the femoral nerve.

Histomorphometric Analysis of Explanted Nerve.

Following perfusion with 4% paraformaldehyde at 16 weeks, femoral nerves were dissected from animals and morphometric analysis was performed according to the standard protocol.

The total number of myelinated axons per nerve cross section, raw tissue area, cross-sectional area of the regenerating cable, and the % nerve regeneration were measured with ImageJ. Axonal (inside the myelin sheath) and nerve fiber (including the myelin sheath) diameters were measured in a random sample from each section.

Western Blot Analysis of Nerve Exudates at 1 Week In Vivo.

To evaluate the presence of Schwann cells within nerve conduits, western blot analysis of Schwann cell markers was performed on nerve exudates (Kaewkhaw, et al., Glia 59, 734, 2011). Conduits (n=3) were implanted into the mouse femoral nerve for 1 week after which animals were sacrificed and nerve exudates within the conduits were removed and run on an SDS-PAGE gel (Invitrogen) and transferred to PVDF membranes (Biorad). Membranes were blocked and probed with antibodies against S100β (1:1000), glial fibrillary acidic protein (GFAP, 1:50,000), GAPDH (1:1000), and β-actin (1:5000) (Abcam) and detected through HPR luminescence of secondary antibodies. Densitometric analysis was performed to quantify band density of GFAP, S100β, and actin from the western blot using ImageJ (NIH). Amounts were normalized based on actin loading control.

Morphological Analysis of Fibrin Matrix Formation.

Animals (n=3 per condition) were sacrificed at 2 weeks postimplantation to visualize the presence of fibrin strands. Nerve explants were postfixed in osmium tetroxide and embedded in resin according to the standard protocol. Longitudinal 1-mm-thick sections of the nerve were cut and stained with 1% toluidine blue/1% borax in distilled water. Conventional light microscopy was used to visualize the presence and orientation of the fibrin matrix.

Statistical Analysis.

The study was designed to allow comparison of the effects of polymers of 89.5 mol % DTE-10 mol % DT-0.5 mol % PEG 1K polymer and PE in both a 2D and conduit fashion on nerve regeneration. Variance analysis using a one-way analysis of variance was used followed by post hoc planned comparisons with the Tukey's test. Differences were considered significant at p<0.05.

Results

In Vitro Characterization

Both PE and 89.5 mol % DTE-10 mol % DT-0.5 mol % PEG 1K polymer nonporous conduits had a similar appearance based on SEM micrographs (FIG. 2A, D, C, F). The porous 89.5 mol % DTE-10 mol % DT-0.5 mol % PEG 1K polymer conduits had an interconnected pore structure, and the degree of porosity and mean pore size of the conduits were 55.2%-1.2% and 35.7-9.0 mm, respectively (FIG. 2B, E). The conduits fabricated from E10-0.5(1K) are opaque, nonflexible (at the 5 mm lengths), have an internal diameter of 580 mm and an external diameter of 680 mm. All conduits remained intact throughout the study. Material and cell studies revealed disparate properties among the conduit types. The response of motor neurons to the different materials was assessed on 89.5 mol % DTE-10 mol % DT-0.5 mol % PEG1K polymer and PE 2D films coated with PLL and laminin. Longer axons were observed on 89.5 mol % DTE-10 mol % DT-0.5 mol % PEG 1K polymer when compared to PE (FIG. 3), as indicated by the peak shift of 89.5 mol % DTE-10 mol % DT-0.5 mol % PEG 1K polymer to the right of the PE and control substrate peaks. An assessment of Schwann cell attachment and extension of processes on the differing substrates revealed that 89.5 mol % DTE-10 mol % DT-0.5 mol % PEG 1K polymer similarly promoted these aspects as compared to PE (FIG. 3B, C). The adsorption of proteins essential to nerve regeneration to the different materials was also significantly different (FIG. 4). The amounts of three ECM proteins adsorbing to 89.5 mol % DTE-10 mol % DT-0.5 mol % PEG 1K polymer were significantly greater compared to PE films.

In Vivo Evaluation

Motor function recovery. Functional recovery was quantified by SFMA of the FBA and PLR (FIG. 5 A-D), using well-established methods (Irintchev, et al., Eur J Neurosci 22, 802, 2005. By week 8, animals that received 89.5 mol % DTE-10 mol % DT-0.5 mol % PEG 1K polymer conduits showed a marked improvement in the FBA as compared to mice that received NP-PE conduits (FIG. 5E). Improvement of motor function in 89.5 mol % DTE-10 mol % DT-0.5 mol % PEG 1K polymer-treated animals was also demonstrated by the PLR, irrespective of whether porous or nonporous conduits were used, by as early as 2 weeks (FIG. 5G). Results collected up to 15 weeks demonstrate the PLR value for animals with 89.5 mol % DTE-10 mol % DT-0.5 mol % PEG 1K polymer conduits approached pre-surgical values at a faster rate than animals treated with NP-PE.

Calculation of the RI further supported that recovery promoted by 89.5 mol % DTE-10 mol % DT-0.5 mol % PEG 1K polymer was enhanced over that promoted with PE conduits. Animals that received 89.5 mol % DTE-10 mol % DT-0.5 mol % PEG 1K polymer conduits achieved RI values approaching 50% for the FBA (FIG. 5F) and 100% for the PLR (FIG. 5H). Animals that received NP-PE conduits demonstrated an average RI value for the FBA of −26% and an average RI value of 23% for the PLR. The tight grouping of the animals within each 89.5 mol % DTE-10 mol % DT-0.5 mol % PEG 1K polymer group indicates consistent performance in contrast with the variation in the RI values calculated from animals receiving NP-PE conduits. Overall, the functional results indicate that the use of an 89.5 mol % DTE-10 mol % DT-0.5 mol % PEG 1K polymer conduit results in significant recovery of functional movement, irrespective of 89.5 mol % DTE-10 mol % DT-0.5 mol % PEG 1K polymer conduit porosity.

Histomorphometric Analysis.

At the endpoint of the study, nerves were analyzed for histomorphometric features (FIG. 6). A significantly greater number of axons were present within regenerating nerve cables formed within 89.5 mol % DTE-10 mol % DT-0.5 mol % PEG 1K polymer conduits with a smaller area of raw fibrous tissue, regardless of the presence of pores in the outer walls. The cross-sectional area of the myelinated nerve fibers was significantly greater in all 89.5 mol % DTE-10 mol % DT-0.5 mol % PEG 1K polymer conduits as compared to the NP-PE conduit, and a greater percentage of this area was occupied by myelinated nerve fibers. Representative 100× images of 1-mm-thick cross sections postfixed in osmium tetroxide as well as the fiber diameter distribution from each condition are shown in FIG. 7. 89.5 mol % DTE-10 mol % DT-0.5 mol % PEG 1K polymer conduits generated nerve cables with a large number of axons, fascicular structures, a large range of nerve fiber diameters, and little fibrous tissue, while the NP-PE conduits contained few, if any, evident axons. The inner lumina were completely filled with what appeared to be dense, fibrous tissue.

Early Differences in Nerve Repair Between Conduit Materials.

The initial formation of a fibrin cable helps support axonal in-growth and Schwann cell infiltration and is crucial for determining at an early time point the final outcome of the regenerating nerve cable. We found that longitudinal fibrin strands could be observed 2 weeks post-implantation in 89.5 mol % DTE-10 mol % DT-0.5 mol % PEG 1K polymer conduits (as indicated by the black arrow in FIG. 8A), but not in NP-PE conduits (FIG. 8A, B), suggesting the initiation of the formation of a fibrin cable across the nerve gap (Zhao, et al., Restor Neurol Neurosci 5, 197, 1993.) Furthermore, western blot analysis of Schwann cell markers within nerve exudates 1 week post-implantation revealed a greater abundance of S100β and GFAP immunoreactivities in exudates removed from 89.5 mol % DTE-10 mol % DT-0.5 mol % PEG 1K polymer conduits as compared to exudates removed from within NPPE conduits (FIG. 8C, D).

Example 2

Materials and Methods
Polymer Synthesis and Characterization

Studies were conducted using a tyrosine-derived polycarbonate to generate the fibers via melt extrusion. A single polymer composition, poly(desaminotyrosyl-tyrosine ethyl ester carbonate), referred to as poly(DTE carbonate) and abbreviated as "E0000", was selected for the study. Poly (DTE carbonate) degrades very slowly in vivo, requiring over one year before significant changes in molecular weight are apparent. Conduits composed of poly(DTE carbonate) will therefore experience only negligible degradation within the time span of our studies and effectively remove degradation as a variable in conduit performance.

Poly(DTE carbonate), was synthesized and purified utilizing previously published procedures (Ertel et al., J Biomed Mater Res 1994; 28(8):919-30). Molecular weights (number average, $M_n$, weight average, $M_w$,) and polydispersity index (PDI) were determined using gel permeation chromatography (GPC, Waters Corporation, Milford, Mass.) relative to polystyrene standards in dimethylformamide containing 0.1% trifluoroacetic acid as the mobile phase. The glass transition temperatures ($T_g$) of the polymers were determined as described before (Engelberg et al., Biomaterials 1991; 12(3):292-304). Poly(DTE carbonate) used to fabricate braided conduits and dipcoated conduits had a $M_n$ of 167,700 Da with a PDI of 1.47 and $T_g$ of 96.5° C. The electrospun coatings were fabricated using E1001(1 k), a copolymer consisting of 89 mol % desaminotyrosyl-tyrosine ethyl ester (DTE), 10 mole percent desaminotyrosyl-tyrosine (DT) and 1 mol % 1 kDa poly(ethylene glycol) (PEG). E1001(1 k) was synthesized using previously published procedures (Magno et al., Journal of Materials Chemistry 2010; 20(40):8885-8893) and had a $M_n$ of 239,000 Da with a PDI of 1.6 and $T_g$ of 97.0° C.

Braided Conduit Fabrication

Different braid designs were initially implemented using 60 μm thick industrial polypropylene (PP) prototype yarn (ATEX Technologies Inc, Pinebluff, N.C.) to determine the effect of braid pattern and fiber density on the conduit pore size and mechanical properties. The following methodologies were utilized for fabricating conduits: A) Single-fiber braid: 24 carriers, 1 PP fiber/carrier, 2/2 braid; B) Triaxial braid: 24 carriers, 3 twisted PP fibers/carrier+4 longitudinal triaxial fibers; C) Three-fiber braid: 24 carriers, 3 twisted PP fibers/carrier, 2/2 braid; D) Three-fiber braid: 24 carriers, 3 twisted E0000 fibers/carrier, 2/2 braid.

Braided conduits used for in vitro and in vivo tests were fabricated by tubular braiding of poly(DTE carbonate) fibers. Poly(DTE carbonate) was melt extruded to yield fibers of a target diameter of about 60 microns using a ⅜ inch single-screw extruder (microextruder from Randcastle, Cedar Grove, N.J.) and monitored using a laser micrometer (Z-Mike 1200 series, Groβ-Umstadt, Germany). The final extruded fiber diameter ranged between 80 and 110 μm and the post fabrication $M_n$ was 138,550 Da with a PDI of 2.05. Three polymer fibers were then twisted together to form a multi-filament yarn and spooled onto braiding spindles. A Herzog NG 1/24-120 tubular braiding machine (Herzog Maschinenfabrik, Oldenburg, Germany) equipped with 24 carriers was used to braid conduits over a Teflon mandrel with an outer diameter of 1.5 mm (Applied Plastics Co., Inc., Norwood, Mass.). After braiding, conduits were cut to desired lengths and ends were trimmed and sealed using a thermocutter (ZTS 20, AZ Zangl, Germany). Conduits were cleaned by sequential washes in cyclohexane (1×), 0.5 volume percent Tween20 in deionized water (1×) and DI water (5×) while being sonicated.

Dipcoated Conduit Fabrication

Conduits were fabricated via dip-coating from a 20% (w/v) poly(DTE carbonate) solution in methylene chloride using previously published procedures (Ezra et al., Tissue Eng Part A 2013), deposited on a 1.5 mm OD Teflon-coated mandrels.

Electro Spinning

Secondary electrospun layers were formed on the braided conduits on rotating mandrels in an electrospinning setup using a high voltage power supply (Gamma High Voltage Research Inc., Omaha Beach, Fla.) and a syringe pump (KD Scientific, Holliston, Mass.) connected to blunt tipped 23 G stainless steel needles via 20 gauge×3' Teflon tubing (both from Hamilton Company, Reno, Nev.). 10% (w/v) polymer solution of 89 mol % DTE-10 mol % DT-1.0 mol % PEG 1K polymer was prepared in glacial acetic acid (Fisher Scientific, Pittsburgh, Pa.) using a 1:25 ratio of trans-4-hydroxy-L-proline (tHyp): 89 mol % DTE-10 mol % DT-1.0 mol % PEG 1K polymer to eliminate beading from the electrospun fibers. Electrospinning was continued until a 300 μm thick coating was formed around the braided conduits. Conduits were thoroughly dried in the fume hood to remove residual solvent.

Hyaluronic Acid (HA) Hydrogel Coating

Sterile braided conduits were dipcoated in a 1% (w/v) sterile thiol-modified hyaluronan solution (HyStem) followed by immediate cross-linking by dipcoating in a sterile 1% (w/v) poly(ethylene glycol diacrylate) (PEGDA) solution (both from Glycosan Biosystems-BioTime, Inc. Alameda, Calif.) in a sonicated water bath. Conduits were dried for 5 minutes after each dipcoating step and the process was repeated for a total of five times. Conduits with dual electrospun and HA coating were also fabricated by first depositing the electrospun layer on the braided conduits as described above, followed by dipcoating in hyaluronan and PEGDA solutions. HA-coated conduits were dried overnight in the laminar flow hood and implanted in dry state for in vivo experiments.

Sterilization

To reduce the bioburden, all conduits were exposed to UV irradiation for 40 minutes prior to in vivo use.

Scanning Electron Microscopy (SEM)

Pore size and topography of sputter-coated (SCD 004 sputter coater, 30 milliAmps for 120 seconds with Au/Pd) specimens was evaluated using SEM (Amray 1830I, 20 kV). Pore size, braid angle and wall thickness of conduits, and the fiber diameter of electrospun mats were measured on SEM images using ImageJ (public domain software from National Institutes of Health). Braid angle was measured between a line perpendicular to the longitudinal axis of the braid and a line parallel to the groups of fibers aligned close to the tube-axis.

Mechanical Testing

Mechanical properties of braided conduits were characterized by compressive and three-point bending tests using a Syntec 5/D mechanical tester, and tensile tests using a MTS Tytron™ 250 Microforce Testing System (both from MTS, Eden Prairie, Minn.). Samples were preconditioned by incubation in PBS at 37° C. overnight and tested immediately after removal from the incubator. Compression tests were performed on 1 cm long conduits, with a transverse crosshead speed of 6 mm/min to the endpoint displacement equivalent to 60% of initial conduit diameter. The compressive stiffness was calculated from the slope of the linear region in the force vs. displacement curves.

Three-point bending tests were performed on 1.5 cm long conduits placed on the lower holder beams of the bending apparatus, which were set 1 cm apart. The third point was lowered from above the midpoint of the conduit at a crosshead speed of 10 mm/min. For tensile testing, 3 cm long conduits were secured in the grips, with a grip separation of 2 cm and stretched at a speed of 20 mm/min until failure. Kink tests were performed by bending 3 cm long conduits on a flexible 0.6 mm diameter wire (Applied Plastics Co., Inc., Norwood, Mass.) until a kink occurred, which was defined as visually detectable reduction in the conduit outer diameter at the point of bending. Poly(DTE carbonate) conduits fabricated by braiding and dipcoating as well as commercially available NeuraGen® conduits (Integra LifeSciences Corporation, Plainsboro, N.J.) were bent and kink formation at the bending point was observed. The angle between the bent arm of the conduits and the horizontal axis was measured and reported as the bending angle. For braided conduits, kink test was carried out further by bending the conduit in a loop until a kink occurred. For this test, braided conduits were gradually twisted into smaller loops and photographed at each increment. The perimeter of the inner loop formed by the conduit was then measured using ImageJ software and the corresponding internal loop diameter was calculated from the perimeter, assuming a circular loop.

In Vivo Evaluation

All experiments were conducted under an approved protocol of the Rutgers Animal Care and Facilities Committee and the Institutional Animal Care and Use Committee (IACUC).

Subcutaneous Implantation of Braided Conduits

Male Sprague-Dawley rats weighing 250-300 g (Charles River Labs, Wilmington, Mass.) were anesthetized by intraperitoneal injection of ketamine/xylazine (75/10 mg/kg, respectively) and braided conduits were implanted in four subcutaneous pockets on the animals' backs. Animals were sacrificed 3 weeks after implantation, and conduits were explanted with the surrounding connective tissue. Immediately after explantation, conduits were fixed in 10% buffered formalin, followed by tissue processing and paraffin embedding for histological staining. Six µm sections were prepared and stained with Hematoxylin&Eosin (H&E) using standard methods.

In Situ Implantation of Conduits in the 1 cm Rat Sciatic Nerve Model:

Female Lewis rats weighing 200-250 g (Charles River Labs, Wilmington, Mass.) were anesthetized by intraperitoneal injection of ketamine/xylazine (75/10 mg/kg, respectively) and implanted with conduits, using published protocols. For the conduit groups a 5 mm section of the sciatic nerve was removed and the nerve stumps were allowed to retract to form a 10 mm gap. Sterile conduits (1.2 cm long and 1.5 mm in diameter) were then sutured to the nerve stumps using two 9-0 perineurial sutures on each end, maintaining the 10 mm gap between the stumps. In the case of autografts, a 1 cm segment of nerve was removed, reversed and sutured back in the gap using three to four 9-0 sutures on each end.

Electrophysiology:

Recovery of the electrophysiological function after nerve injury was evaluated under general anesthesia by measuring the compound muscle action potentials (CMAPs) at the dorsal and plantar foot muscles, which are the most distal targets of the peroneal and tibial branches of the sciatic nerve. CMAPs were recorded immediately before surgery (intact animals) and every 4 weeks after surgery using the VikingQuest EMG system (Natus Medical Inc., San Carlos, Calif.). Subcutaneous EEG needles were used as recording, reference and ground electrodes. Reference and ground electrodes were placed at the lateral side 5th metatarsal and heal calcaneus, respectively on the operated side of the rat. Recording electrode was inserted subcutaneously on the dorsal foot muscle over the 3rd metatarsal for the peroneal CMAP, and on the plantar muscle for the tibial CMAP. The sciatic nerve was stimulated percutaneously using a bipolar stimulating electrode at the ankle level directly posterior to the tibia. Electrodes were adjusted locally to produce maximal CMAP amplitude and the stimulus was increased incrementally to produce a supramaximal response. The average of three consecutive CMAP amplitudes, measured from the onset of the CMAP signal to the top of the peak, and three consecutive latencies were calculated for each animal and averaged for the animals in the same treatment group for plotting.

Histomorphometric Analysis of Explanted Nerves

Sixteen weeks after surgery, rats were deeply anesthetized using ketamine/xylazine anesthesia, the sciatic nerve on the operated side was exposed and in-situ fixation of the nerve was performed by immersing the nerve in Trump's fixative for 30 minutes. The nerve was then harvested and processed as described previously. Total numbers of myelinated axons per nerve cross-section were counted using ImageJ 1.43u software, by counting a minimum 500 myelinat-ed axons in random 100× images for each 1 µm thick nerve section and averaging over three replicate nerve sections. The raw tissue area, cross-sectional area of the myelinated nerve cable, and the % nerve regeneration were measured on the 10× images and analyzed with ImageJ 1.43u software. Axonal (inside the myelin sheath) and nerve fiber (including the myelin sheath) dia-meter were measured in three random 100× samples from each section to calculate the G-ratio.

Muscle Harvest

Upon nerve harvest, animals were euthanized by $CO_2$ asphyxiation. The tibialis anterior and gastrocnemius muscles of both hind limbs were immediately harvested by exposing the musculature via a knee to ankle longitudinal skin incision. The muscles were harvested from origin to insertion and weighed with an electronic balance.

Statistical Methods

Data in this study are represented as mean±SE unless otherwise indicated. One-way analysis of variance (ANOVA) tests with Dunnett's post hoc tests were used in this study to assess significant differences. Statistical significance was defined as $p<0.05$.

Results

Conduit Fabrication and Physical Characterization

Three conduit prototypes were constructed by varying the number of filaments and twists in a yarn using commercially available non-degradable polypropylene prototyping fibers. The resulting conduits indeed showed substantial differences in physical characteristics, such as pore size and braid angle. A 2/2 braid constructed from three-fiber yarn had the most favorable mechanical features, demonstrating superior kink resistance and elastic deformation. Triaxial braids had the lowest pore size, were stiffer and possessed undesirable shape memory upon deformation. Owing to a combination of pore size and mechanical properties, the traditional 2/2 braiding method was selected to explore in more detail using poly(DTE carbonate) fibers. Poly(DTE carbonate) braided conduits were fabricated with 80 to 110 µm diameter fibers. The resulting conduits had an average pore size of 65±19 µm and a 1.5 mm inner lumen diameter.

Mechanical Comparison of Braided Conduits

For repair of large nerve gaps in areas of high mobility, flexibility and prevention of kinking are important conduit design criteria. We compared the mechanical properties of braided poly(DTE carbonate) conduits, non-porous dipcoated poly(DTE carbonate) conduits, with 183±15 µm thick walls, and the clinically used NeuraGen® conduits consisting of collagen I (Integra Lifesciences, South Plainfield, N.J.). Due to the inability to secure a sufficient quantity of the NeuraGen® conduits, not all experiments could be replicated and the previous findings of Yao, et al. using these conduits are sometimes cited to complete the comparison.

To assess the capacity to withstand flexation while maintaining an open lumen, kink tests were performed to assess the angle to which the poly(DTE carbonate) conduits can be bent before any luminal occlusion occurs. Conduits were bent on a wire until a kink, which is a reduction of the lumen inner diameter, occurred. For the dipcoated conduits and NeuraGen®, a visible collapse in lumen diameter occurred when the conduits were bent 29.3° and 55.0°, respectively, from the horizontal axis. Braided conduits resisted kinking, maintained constant lumen diameter when bent at angles exceeding 125°. Braided conduits also resumed their original shape after release of the load, whereas dipcoated and NeuraGen® conduits partially or completely occluded the lumen when bent and did not resume their original shape.

These results indicate that our braided conduits are highly resistant to luminal occlusion and are much more likely to maintain an open lumen when applied in areas of high flexation. The large flex angles allowed by the braided conduits are physiologically relevant; elbows and finger joints routinely bend at high angles well in excess of 90°. Failure due to breakage near the knee joint has been reported for 22 mm long collagen tubes that were used in the rat sciatic nerve injury model due to insufficient flexibility of tubular constructs.

Peripheral nerves also experience tensile, compressive and shear forces created by the limb movement and muscular contraction. Peripheral nerves are under tensile loads in situ and experience ~11% strain in resting position. While tolerating 11.7 MPa maximum tensile stress. Therefore, any nerve conduit that acts to bridge a peripheral nerve gap should be able to reversibly elongate under loads up to 11.7 MPa. We found this load is within the linear portion of the stress-strain curve of the poly(DTE carbonate) braided conduits, which show 17-22% reversible strain under this load, sufficient to withstand the stress of limb movements.

In transverse compression, the dipcoated conduits displayed the most resistance to the applied load but plastically deformed when compressed to 60% of the inner diameter, while the braided conduits regained their original shape immediately after removing the compressive load. The reported data of the NeuraGen® conduits indicates that under compression these conduits deform 10-fold more than the braided conduits. Similar trends were noted for three point-bending experiments for dipcoated and braided conduits, with dipcoated conduits showing greater resistance to bending. No bending data was reported on the NeuraGen® conduits. This observation that the braided conduits can freely bend, without occluding their lumen is a critical advantage over the other conduits that are either too stiff to bend, and thus may cause tissue damage, or result in a kink at the bending point, crushing the newly formed nerve cable. In terms of tensile stiffness, braided and NeuraGen® conduits yielded more readily to tension than the dipcoated conduits, with the braided conduits deforming elastically under physiological loading conditions, which is beneficial for nerves that experience movement and tensile stress. On the other hand, the ultimate tensile strength of the braided conduits was 5-fold higher than NeuraGen® demonstrating the strength of the braided structure against the clinical predicate.

Host Response

A small control study was conducted to ensure that the conduit material does not elicit a strong inflammatory response that could affect the results obtained in the subsequent nerve regeneration studies. To evaluate the gross tissue response, poly(DTE carbonate) braided conduits were implanted into subcutaneous pockets on the backs of adult rats. After 3 weeks, conduits were removed and H&E histology was performed. Sections revealed the expected formation of a fibrous capsule around the conduits. Capsule tissue was diffusely organized and lacked a high concentration of inflammatory cells, indicating that the host response to the poly(DTE carbonate) braided conduit was minimal and in agreement with previous findings on the host-response to polymers within the tyrosine-derived polycarbonate family.

Secondary Coatings

The H&E stain also revealed surrounding tissue adhered to the conduit material, penetrat-ed through the pores and entered into the poly(DTE carbonate) conduit lumen. Effects of conduit pore size on the outcome of nerve regeneration have been investigated and, while results and interpretations of this critical aspect vary widely, the optimal pore size for conduits was reported to be in the 5-30 µm range to enable nutrient and waste diffusion and minimize fibrotic and inflammatory cell infiltration. Poly(DTE carbonate) braided conduits have 20 to 140 µm pores. Due to H&E-stained sections showing infiltration of cells into the braided conduits, we develop-ed temporary micro or nanoporous barrier coatings that would allow for nutrient exchange but reduce the ability of non-nerve cells to infiltrate into the conduit and disrupt regeneration.

Three conduit coatings were explored: a hydrogel coating consisting of cross-linked hyaluronic acid (HA) that was dehydrated after application, a layer of electrospun 89 mol % DTE-10 mol % DT-1.0 mol % PEG 1K polymer applied on the surface of the conduit and a combination of the electrospun layer subsequently coated with HA. We used a high molecular weight and PEGDA cross-linked version of HA that we found to repel the attachment of fibroblasts. The PEGDA cross-linked HA hydrogels are reported to be stable for 4-8 weeks in vivo but to our knowledge have not been used in this manner as a nerve conduit coating.

Average size of the macropores on uncoated braided conduits were 65±19 µm and the secondary coating methods provided varying degrees of coverage on these pores. The thin HA coating was nonporous in its dehydrated state and coated over the braid fibers as well as the pores. The electrospun layer had an average thickness of 292±39 µm with 0.26±0.06 µm fiber diameter and a pore size of 2.02 µm, calculated with the equation for the mean pore radius in isotropic near-planar networks, derived by Sampson et al., assuming a pore fraction of 0.85. For the electrospun and HA-coated conduits, sonicating the conduits while dipcoating allowed for the hydrogel to diffuse through the electrospun fiber mat and thoroughly coat around the fibers of the mat and the underlying conduit to create an apparently non-porous barrier. The electrospun layer shrank upon coating with the HA hydrogel to a final thickness of 54±9 µm. Compression, bending and tensile tests indicated that these coatings did not undermine the mechanical advantages of the braided conduits.

Assessment of Regeneration of the Rat Sciatic Nerve

To evaluate the basic capacity to support nerve regeneration, poly(DTE carbonate) braided conduits were tested in the well described 1 cm gap rat sciatic nerve injury model. Treatment groups included the uncoated braided conduit (n=7 animals/group), braided conduits coated with HA (n=7), braided conduits coated with the electrospun 89 mol % DTE-10 mol % DT-1.0 mol % PEG 1K polymer (n=4), braided conduits coated sequentially with the electrospun 89 mol % DTE-10 mol % DT-1.0 mol % PEG 1K polymer followed by HA (n=4). A control group of an autograft (n=7) inverted within the injury site was used and the regenerated nerves of all groups were collected after 16 weeks.

Histomorphometric Analysis of Explanted Nerve

Sections of the regenerated nerve segments from the center of conduits showed that all conditions supported regeneration of axons, but significant variation was observed. Regenerated tissue within uncoated braided conduits showed many regenerated axons within fascicles that were loosely organized. A considerable amount of non-nerve tissue with a fibrous appearance was observed within the conduit both exterior to the regenerated nerve as well as intercalated between the fascicles located at the periphery of the regenerated nerve. Similar features were noted on nerves that regenerated within braided conduits with an electrospun fiber coating. The nerve cables in electrospun coated braided conduits were smaller in size and variable in the presence of a boundary between axonal area and the surrounding tissue; some samples had loose nerve fascicles while in others, fascicles were more highly packed and the nerve cable was surrounded by loosely arranged layers of non-nerve tissue. This result was surprising and suggests that the electrospun mat surrounding the braided conduit may have facilitated fibrous tissue infiltration.

In contrast, the HA-coated conduits all showed rounded and densely packed nerve cables with tightly packed fascicles and axons. Regenerated nerves within the HA-coated conduits all appear to have formed a perineurial layer forming a distinct boundary between the regenerated nerve and the fibrous tissue within the conduit. These features were not replicated in the nerves regenerated within braided conduits coated with both electrospun fibers and HA where extensive fibrous tissue was observed that had intercalated within the regenerating nerve axons and fascicles. Regenerated nerves within autologous grafts were, as expected, highly organized with a mature perineurium.

Histomorphometric characterization showed that the myelinated area or area occupied by the nerve axons was largest in uncoated braided conduits, which was comparable to autologous grafts. HA-coated conduits showed the next largest myelinated area, followed by electrospun fiber and HA coated conduits, and lastly conduits coated with only the electrospun fibers. In contrast, the axonal density was the highest in HA-coated conduits and lowest in uncoated braided conduits, confirming that HA-coated conduits contained densely regenerated nerve cables while uncoated braided conduits have large but loosely packed nerve cables. Assessment of axonal myelination by measuring the G-ratio showed the smallest G-ratios were present in the autologous group, with all other groups significantly larger from autologous but equivalent to one another. In comparison to the autologous grafts, HA-coated conduits had a greater number of axons packed per unit area even though these axons were less mature (larger G-ratio, thinner myelin sheaths) as expected. Over the course of regeneration, the axons in the HA-coated conduit group will likely mature further to achieve faster nerve conduction and improved regeneration outcomes.

Muscle Weight

Following sciatic nerve bisection, the tibialis anterior (TA) and gastrocnemius muscles atrophy and regain of muscle weight is indicative of recovery. These muscles were harvested from both hind limbs and weighed at the end of the 16-week recovery period. Muscle weight recovery was the greatest with the autologous graft group, followed by the HA-coated braided conduits. The TA muscle weight recovery for the HA-coated braided conduits was significantly higher than the uncoated conduits. TA and gastrocnemius muscle weight recovery were equivalent in the rest of the conduit groups. Improved TA muscle weight recovery with the HA-coated braided conduits supports the findings of the nerve histology in that enhanced regeneration corresponds to limiting the degree of fibrous tissue infiltration and the ability to form a perineurial layer with these conduits.

Electrophysiology

To assess functional nerve regeneration, electrophysiological measurement of nerve conduction through the defect and to reinnervated muscle groups was assessed by recording the compound muscle action potential (CMAP) supramaximal amplitude and latency of the peroneal and tibial nerves. For both tibial and peroneal CMAP, the earliest post-operative CMAP signals were detected by 8 weeks for the autografts and 12 weeks for the conduit groups. 37% of the CMAP signal was recovered in the autograft group at the 16-week end-point, which displayed the largest amplitude among treatments. Among the conduit groups, HA-coated braided conduits had the highest CMAP amplitudes with approximately 14% of the CMAP signal recovered at the 16-week end-point.

Improvement in functional regeneration is evident in the inverse correlation between CMAP latency and amplitudes. Accordingly, the autograft group had the lowest peroneal and tibial latency values at 16 weeks indicating a more rapid signal conduction. Observed latency values were equivalent for the braided conduit groups with the exception of the ES-coated conduits, which displayed longer latencies, in agreement with fewer axons and greater G-ratio observed in the histology of this group.

Electrophysiology supports the histology, indicating a major role of porosity and cell infiltration in hindering nerve recovery following injury. Perhaps most surprising was the negative effect the ES layers with and without HA had on non-nervous tissue infiltration. The present study found these conduits became enriched with fibrous tissue throughout the mats when applied as a coating to the conduits. It is likely that the extensive cell friendly surface area offered by the mats overwhelmed the cell repellent properties of HA. In addition, loosening of the mats due to continuous exposure to the in vivo environment may have also facilitated tissue infiltration. Conduit materials, poly(DTE carbonate) and 89 mol % DTE-10 mol % DT-1.0 mol % PEG 1K polymer were also shown to be friendly to cellular attachment and protein adsorption.

What is claimed is:

1. A biocompatible nerve conduit for nerve re-generation comprising a porous fiber tube coated with a bioresorbable hydrogel, said fibers comprising a biocompatible polymer that supports nerve regeneration by preferential adsorption of endogenous proteins, wherein said fibers are braided with pores in the range from 5 to 200 micrometers using a kink-resistant braiding pattern and said hydrogel coating material and thickness are selected to control the overall porosity such that nutrients and oxygen can diffuse through said hydrogel coating but the infiltration of fibrous tissue through the coating is prevented, wherein:

said biocompatible polymer has repeating units of the structure:

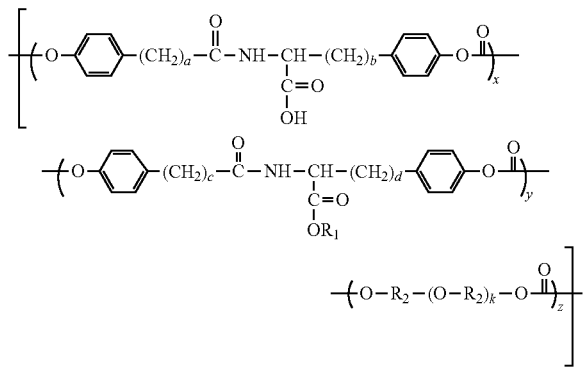

wherein a and b are independently 0 or an integer between 1 and 6, inclusive; c and d are independently 0 or an integer between 1 and 6, inclusive; each $R_1$ is independently selected from the group consisting of straight and branched alkyl groups containing up to 18 carbon atoms; each $R_2$ is independently an alkylene group containing up to 6 carbon atoms; k is between about 20 and about 200; and x ranges between about 0.002 and about 0.20; z ranges between about 0.005 and about 0.01; and x+y+z=1.00.

2. The biocompatible nerve conduit of claim 1, wherein a and b are two and one, respectively.

3. The biocompatible nerve conduit of claim 1, wherein c and d are two and one, respectively, and $R_1$ is ethyl.

4. The biocompatible nerve conduit of claim 1, wherein $R_2$ for said polymer is ethylene and k is between about 20 and about 100.

5. The biocompatible nerve conduit of claim 1, wherein said porous fiber tube comprises a helically wound biaxial braid.

6. The biocompatible nerve conduit of claim 1, wherein said bioresorbable hydrogel comprises cross-linked hyaluronic acid (HA).

7. The biocompatible nerve conduit of claim 6, wherein said hyaluronic acid (HA) is cross-linked with PEGDA.

8. The biocompatible nerve conduit of claim 1, wherein the biocompatible nerve conduit further comprises a second bioresorbable hydrogel for filling the interior lumen of the biocompatible nerve conduit.

9. The biocompatible nerve conduit of claim 8, wherein the second hydrogel comprises collagen with a covalently attached neurite-promoting peptide mimic of the Human Natural Killer-1 (m-HNK-1) glycan.

10. A method for the treatment or repair of a peripheral nerve injury comprising the implantation of the nerve conduit of claim 1, comprising the steps of:
sectioning the injured nerve's proximal and distal stumps cleanly and perpendicularly so that no damages or scarred tissue remains,
placing the conduit in situ so that about 1 mm of each stump can be fitted into the proximal and distal ends of the conduit respectively, and
securing said nerve stumps to said conduit using conventional micro-neurosurgical techniques.

11. The method of claim 10, comprising further stabilizing said conduit to the surrounding soft-tissue with sutures, or by flooding the repair site with fibrin-like adhesive, or both.

12. The biocompatible nerve conduit of claim 1, further comprising a nerve or nerve tissue or nerve cellular component that is inserted into the interior lumen of the biocompatible nerve conduit.

13. The biocompatible nerve conduit of claim 12, wherein said cellular component is injected within a hydrogel to fill said lumen, or are injected into a hydrogel-type filler within the lumen.

14. The biocompatible nerve conduit of claim 12, wherein said tissue component is laid into the lumen after the conduit is slit longitudinally to provide access.

15. The biocompatible nerve conduit of claim 1, wherein the kink-resistant braiding pattern maintains a constant lumen diameter when bent at angles exceeding 125° on a flexible 0.6 mm diameter wire and resume its original shape after release of the bending load.

16. The biocompatible nerve conduit of claim 1, wherein x ranges between about 0.05 and 0.20.

* * * * *

UNITED STATES PATENT AND TRADEMARK OFFICE
CERTIFICATE OF CORRECTION

PATENT NO.        : 10,940,235 B2
APPLICATION NO.   : 15/566552
DATED             : March 9, 2021
INVENTOR(S)       : Joachim Kohn et al.

It is certified that error appears in the above-identified patent and that said Letters Patent is hereby corrected as shown below:

In the Specification

Delete the paragraph under the STATEMENT REGARDING FEDERALLY SPONSORED RESEARCH on Column 1, Line number 16 and replace with the following:

--This invention was made with government support under grant number W81XWH-14-2-0003 awarded by the Defense Health Agency, Medical Research and Development Branch. The government has certain rights in the invention.--

Signed and Sealed this
Twenty-seventh Day of May, 2025

Coke Morgan Stewart
*Acting Director of the United States Patent and Trademark Office*